(12) United States Patent  
Young et al.

(10) Patent No.: US 10,578,548 B2  
(45) Date of Patent: *Mar. 3, 2020

(54) SYSTEMS, APPARATUSES, AND METHODS FOR FLUID ANALYSIS AND MONITORING

(71) Applicant: Virtual Fluid Monitoring Services LLC, Houma, LA (US)

(72) Inventors: Dustin Young, Blanchard, OK (US); Mark Chmielewski, Duluth, MN (US); Chris Morton, Duluth, MN (US)

(73) Assignee: Virtual Fluid Monitoring Services LLC, Houma, LA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/173,200

(22) Filed: Oct. 29, 2018

(65) Prior Publication Data

US 2019/0072483 A1 Mar. 7, 2019

Related U.S. Application Data

(63) Continuation of application No. 15/139,771, filed on Apr. 27, 2016, now Pat. No. 10,151,687.

(Continued)

(51) Int. Cl.
*G01N 21/31* (2006.01)
*G06N 3/08* (2006.01)
(Continued)

(52) U.S. Cl.
CPC ............ *G01N 21/31* (2013.01); *G01N 15/06* (2013.01); *G01N 15/1459* (2013.01);
(Continued)

(58) Field of Classification Search
CPC .... G01N 21/31; G01N 21/3577; G01N 21/85; G01N 21/645; G01N 21/65; G01N 15/06;
(Continued)

(56) References Cited

U.S. PATENT DOCUMENTS 3,751,661 A 8/1973 Packer et al.
3,859,851 A 1/1975 Urbanosky
(Continued)

FOREIGN PATENT DOCUMENTS

GB 2368391 5/2002
JP H04-50639 A 2/1992
(Continued)

OTHER PUBLICATIONS

Knauer et al., "Soot Structure and Reactivity Analysis by Raman Microspectroscopy, Temperature-Programmed Oxidation, and High-Resolution Transmission Electron Microscopy", J. Phys. Chem. v. 113, pp. 13871-13880, 2009.

(Continued)

*Primary Examiner* — Hina F Ayub
(74) *Attorney, Agent, or Firm* — Jason P. Mueller; Adams and Reese LLP

(57) ABSTRACT

Embodiments of the present disclosure provide for systems, apparatuses, and methods for real-time fluid analysis. Embodiments include a removable and replaceable sampling system and an analytical system connected to the sampling system. A fluid may be routed through the sampling system and real-time data may be collected from the fluid via the sampling system. The sampling system may process and transmit the real-time data to the analytical system. The analytical system may include a command and control system that may receive and store the real-time data in a database and compare the real-time data to existing data for the fluid in the database to identify conditions in the fluid.

30 Claims, 18 Drawing Sheets

Related U.S. Application Data

(60) Provisional application No. 62/237,694, filed on Oct. 6, 2015, provisional application No. 62/205,315, filed on Aug. 14, 2015, provisional application No. 62/153,263, filed on Apr. 27, 2015.

(51) Int. Cl.

| | | |
|---|---|---|
| *G06N 3/04* | (2006.01) | |
| *G01N 15/06* | (2006.01) | |
| *G01N 33/28* | (2006.01) | |
| *G01N 35/00* | (2006.01) | |
| *G01N 15/14* | (2006.01) | |
| *G01N 21/3577* | (2014.01) | |
| *G01N 21/85* | (2006.01) | |
| G01N 21/65 | (2006.01) | |
| G01N 21/64 | (2006.01) | |
| G01N 33/18 | (2006.01) | |
| G01N 15/00 | (2006.01) | |
| G01N 1/02 | (2006.01) | |
| G01N 21/35 | (2014.01) | |

(52) U.S. Cl.
CPC ..... *G01N 15/1463* (2013.01); *G01N 21/3577* (2013.01); *G01N 21/85* (2013.01); *G01N 33/2858* (2013.01); *G01N 33/2876* (2013.01); *G01N 33/2888* (2013.01); *G01N 35/00871* (2013.01); *G06N 3/04* (2013.01); *G06N 3/08* (2013.01); *G01N 1/02* (2013.01); *G01N 21/645* (2013.01); *G01N 21/65* (2013.01); *G01N 33/18* (2013.01); *G01N 33/28* (2013.01); *G01N 2015/0065* (2013.01); *G01N 2015/0088* (2013.01); *G01N 2015/0693* (2013.01); *G01N 2021/3595* (2013.01); *G01N 2035/00881* (2013.01); *G01N 2201/062* (2013.01); *G01N 2201/12* (2013.01)

(58) Field of Classification Search
CPC ........... G01N 15/1459; G01N 15/1463; G01N 33/2858; G01N 33/2876; G01N 33/2888; G01N 33/18; G01N 33/28; G01N 35/00871; G01N 3/04; G01N 3/08; G01N 2015/0065; G01N 2015/0088; G01N 2015/0693; G01N 2021/3595; G01N 2035/00881; G01N 2201/062; G01N 2201/12

See application file for complete search history.

(56) References Cited

U.S. PATENT DOCUMENTS

| | | | |
|---|---|---|---|
| 4,396,259 A | 8/1983 | Miller | |
| 4,963,745 A | 10/1990 | Maggard | |
| 4,994,671 A | 2/1991 | Safinya et al. | |
| 5,139,334 A | 8/1992 | Clarke | |
| 5,161,409 A | 11/1992 | Hughes et al. | |
| 5,167,149 A | 12/1992 | Mullins et al. | |
| 5,194,910 A | 3/1993 | Kirkpatrick, Jr. et al. | |
| 5,201,220 A | 4/1993 | Mullins et al. | |
| 5,266,800 A | 11/1993 | Mullins | |
| 5,331,156 A | 7/1994 | Hines et al. | |
| 5,349,188 A | 9/1994 | Maggard | |
| 5,360,738 A | 11/1994 | Jones et al. | |
| 5,497,008 A | 3/1996 | Kumakhov | |
| 5,557,103 A | 9/1996 | Hughes et al. | |
| 5,598,451 A | 1/1997 | Ohno et al. | |
| 5,604,441 A * | 2/1997 | Freese, V | G01N 27/221 324/663 |
| 5,684,580 A | 11/1997 | Cooper et al. | |
| 5,701,863 A | 12/1997 | Cemenska et al. | |
| 5,717,209 A | 2/1998 | Bigman et al. | |
| 5,739,916 A | 4/1998 | Englehaupt | |
| 5,751,415 A | 5/1998 | Smith et al. | |
| 5,754,055 A | 5/1998 | McAdoo et al. | |
| 5,859,430 A | 1/1999 | Mullins et al. | |
| 5,939,717 A | 8/1999 | Mullins | |
| 5,982,847 A | 11/1999 | Nelson | |
| 5,986,755 A | 11/1999 | Ornitz et al. | |
| 5,999,255 A | 12/1999 | Dupee et al. | |
| 6,028,667 A | 2/2000 | Smith et al. | |
| 6,100,975 A | 8/2000 | Smith et al. | |
| 6,274,865 B1 | 8/2001 | Schroer et al. | |
| 6,289,149 B1 | 9/2001 | Druy et al. | |
| 6,350,986 B1 | 2/2002 | Mullins et al. | |
| 6,452,179 B1 | 9/2002 | Coates et al. | |
| 6,474,152 B1 | 11/2002 | Mullins et al. | |
| 6,507,401 B1 | 1/2003 | Turner et al. | |
| 6,707,043 B2 | 3/2004 | Coates et al. | |
| 6,734,963 B2 | 5/2004 | Gamble et al. | |
| 6,753,966 B2 | 6/2004 | Von Rosenberg | |
| 6,775,162 B2 | 8/2004 | Mihai et al. | |
| 6,779,505 B2 | 8/2004 | Reischman et al. | |
| 6,897,071 B2 | 5/2005 | Sonbul | |
| 6,956,204 B2 | 10/2005 | Dong et al. | |
| 6,989,680 B2 | 1/2006 | Sosnowski et al. | |
| 7,043,402 B2 | 5/2006 | Phillips et al. | |
| 7,095,012 B2 | 8/2006 | Fujisawa et al. | |
| 7,391,035 B2 | 6/2008 | Kong et al. | |
| 7,581,434 B1 | 9/2009 | Discenzo et al. | |
| 7,589,529 B1 | 9/2009 | White et al. | |
| 7,842,264 B2 | 11/2010 | Cooper et al. | |
| 7,855,780 B1 | 12/2010 | Djeu | |
| 7,938,029 B2 | 5/2011 | Campbell et al. | |
| 8,018,596 B2 | 9/2011 | Salerno et al. | |
| 8,155,891 B2 | 4/2012 | Kong et al. | |
| 8,781,757 B2 | 7/2014 | Farquharson et al. | |
| 9,261,403 B2 | 2/2016 | Walton et al. | |
| 9,341,612 B2 | 5/2016 | Gorritxategi et al. | |
| 9,606,063 B2 | 3/2017 | Lee et al. | |
| 2002/0030868 A1 | 3/2002 | Salomaa | |
| 2002/0113961 A1 | 8/2002 | Gamble et al. | |
| 2004/0046121 A1 | 3/2004 | Golden et al. | |
| 2004/0241045 A1 | 12/2004 | Sohl et al. | |
| 2006/0053005 A1 | 3/2006 | Gulati | |
| 2006/0169033 A1 | 8/2006 | Discenzo | |
| 2006/0283931 A1 | 12/2006 | Polli et al. | |
| 2007/0078610 A1 | 4/2007 | Adams et al. | |
| 2007/0143037 A1 | 6/2007 | Lundstedt et al. | |
| 2009/0211379 A1 * | 8/2009 | Reintjes | G01N 1/14 73/863.23 |
| 2010/0255518 A1 | 10/2010 | Goix et al. | |
| 2011/0155925 A1 | 6/2011 | Ukon et al. | |
| 2011/0198500 A1 | 8/2011 | Hotier et al. | |
| 2011/0261354 A1 | 10/2011 | Sinfield et al. | |
| 2013/0050696 A1 | 2/2013 | Antunovich et al. | |
| 2014/0188404 A1 | 7/2014 | Von Herzen et al. | |
| 2014/0188407 A1 | 7/2014 | Von Herzen et al. | |
| 2014/0212986 A1 | 7/2014 | Angelescu et al. | |
| 2014/0229010 A1 | 8/2014 | Farquharson et al. | |
| 2015/0211971 A1 | 7/2015 | Little, III et al. | |
| 2015/0300945 A1 | 10/2015 | Gao et al. | |
| 2016/0069743 A1 | 3/2016 | McQuilkin et al. | |
| 2016/0187277 A1 | 6/2016 | Potyrailo et al. | |
| 2016/0195509 A1 | 7/2016 | Jamieson et al. | |
| 2016/0313237 A1 | 10/2016 | Young et al. | |
| 2016/0363728 A1 | 12/2016 | Wang et al. | |
| 2017/0016843 A1 | 1/2017 | Gryska et al. | |
| 2017/0234819 A1 | 8/2017 | Lilik et al. | |

FOREIGN PATENT DOCUMENTS

| | | |
|---|---|---|
| JP | H04-77648 | 3/1992 |
| JP | H09-138196 A | 5/1997 |
| JP | 2000-509155 A | 7/2000 |
| JP | 2003-534528 A | 11/2003 |
| JP | 2004020412 | 1/2004 |
| JP | 2011-133370 A | 7/2011 |
| JP | 2012-112759 A | 6/2012 |
| JP | 2012-136987 A | 7/2012 |
| JP | 2013170873 A | 9/2013 |

(56) References Cited

FOREIGN PATENT DOCUMENTS

| JP | 2014-130141 A | 7/2014 |
|---|---|---|
| RU | 2516200 C2 | 5/2014 |
| WO | 0136966 | 5/2001 |

OTHER PUBLICATIONS

Feraud et al., "Independent Component Analysis and Statistical Modelling for the Identification of Metabolomics Biomarkers in 1H-NMR Spectroscopy", Journal of Biometrics & Biostatistics, vol. 8, issue 4, pp. 1-8, 2017.

"Raman Applications Throughout the Petroleum Refinery Blending to Crude Unit", Apr. 26, 2018, APACT Conference, Newcastle, United Kingdom.

Gebarin S. | On-line and In-line Wear Debris Detectors: What's Out There? On-line article, https://machinerylubrication.com/Articles/Print/521.

Cheng B. et al | "Thermal Oxidation Characteristic of Ester Oils Based on Raman Spectroscopy".

Cooper D.| "SFG Spectroscopy is Key to Oil Industry Research", Phonics Spectra, Mar. 2014.

"Accurate and Dependable Choice for In-Service Oil and Fuel Analysis", https://www.azom.com/article.aspx? ArticleID=14948.

Ge , et al | "Raman Spectroscopy of Diesel and Gasoline Engine-Out Soot Using Different Laser Power" www.researchgate.net/publication/328528476.

"Breakthrough study opens door to broader biomedical applications for Raman spectroscopy", Feb. 19, 2013, by IOS Press.

"Breakthrough study opens door to broader biomedical applications for Raman spectroscopy", by IOS press, Feb. 19, 2013. https://phys.org/news/2013-02-breakthrough-door-broader-biomedical-applications.html.

* cited by examiner

SYSTEMS, APPARATUSES, AND METHODS FOR FLUID ANALYSIS AND MONITORING

CROSS-REFERENCE TO RELATED APPLICATIONS

This application is a continuation of U.S. Non-Provisional application Ser. No. 15/139,771, filed Apr. 27, 2016, which claims the benefit of U.S. Provisional Patent Application Nos. 62/153,263, filed Apr. 27, 2015, 62/205,315, filed Aug. 14, 2015, and 62/237,694, filed Oct. 6, 2015, all of which are incorporated herein by reference.

DESCRIPTION OF EMBODIMENTS

Figure 1:
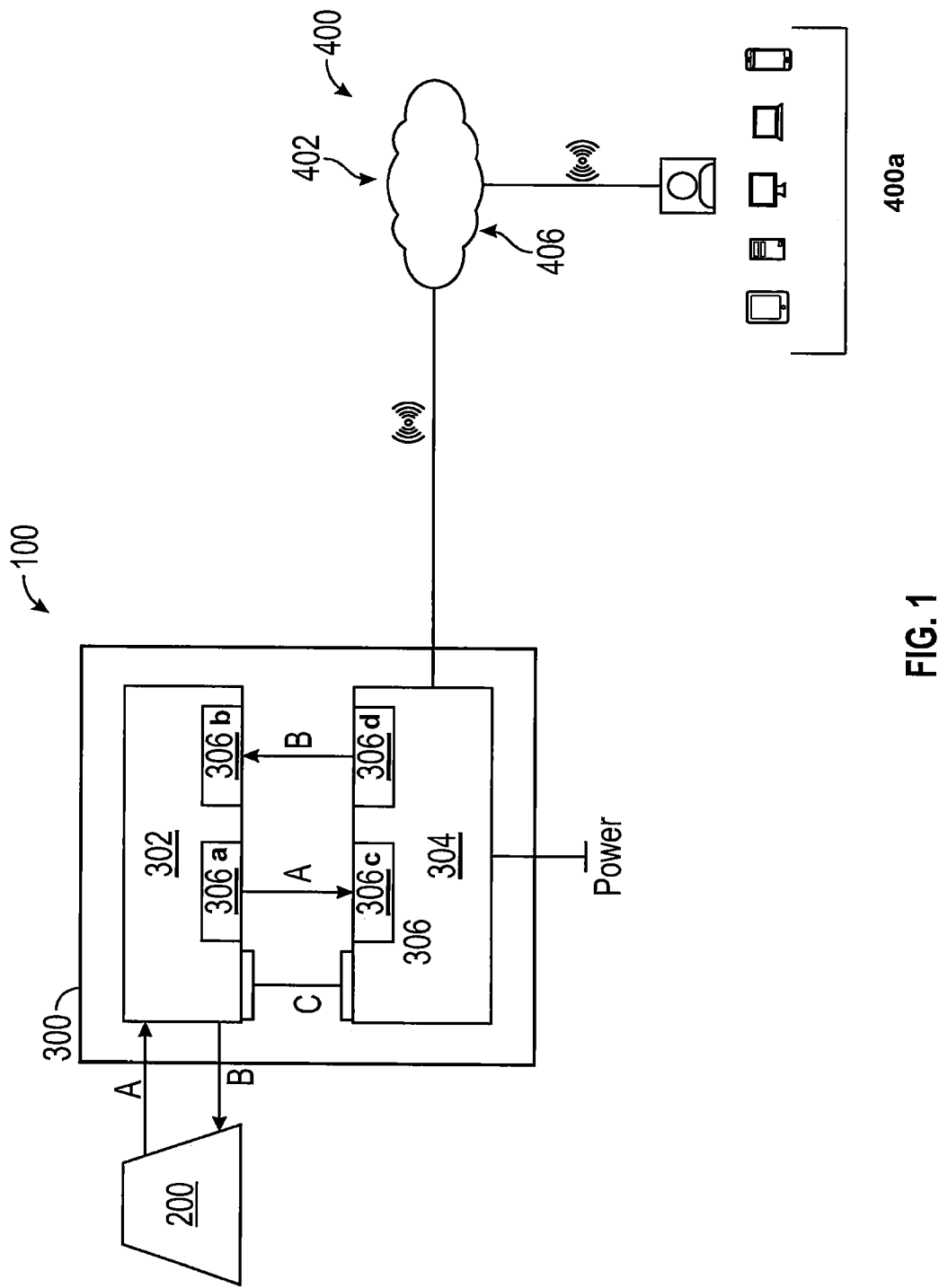
FIG. 1 is a schematic of a fluid analysis system, according to an exemplary embodiment of the present disclosure.

Current fluid analysis systems, including oil and water analysis systems, are inefficient, inaccurate, slow, and/or expensive to maintain. Particularly, in current oil analysis systems: over 50% of oil analysis sample readouts may be returned as inconclusive; extraction of oil samples may lead to contamination of the samples such that the results may be inaccurate; analysis reporting may take as long as seven to ten days after the sample is drawn and lead to "stale" results, thereby minimizing a user's opportunity for preventative action; sampling methods may require the use, storage, and disposal of plastic bottles as well as the oil samples, which may have a negative environmental impact; samples may typically have to be shipped to a lab which may increase costs and delays; analysis capabilities on each oil sample may be limited to measuring wear metals and viscosity; thorough analysis and reporting may be exponentially more expensive, leading to delays between drawing the sample and receiving the report, along with additional related costs; and in most current systems, equipment users do not have a consistent or effective method for storing and managing the data gathered from each analysis, so the opportunity to identify trends or inherent deficiencies in the analysis may be lost.

Oil analysis systems for engine oil may involve additional complexities in that the oil being analyzed may include several contaminants produced by the engine when in operation that may lead to engine damage. These contaminants include solids (carbon), liquids (moisture), and gases that may lead to thermal breakdown of the engine oil, resulting in less protection of engine components and eventual wear and failure of engine parts. Thermal breakdowns occur when the build-up of solid, liquid, and/or gaseous contaminants from the combustion process change the molecular structure of engine oil, leading to an increase in the oil's viscosity.

Similarly, current water analysis systems either have several limitations or are virtually non-existent. These limitations are evident from the recent water crisis in Flint, Mich., as well as the recurring (and slow responses to) water boil advisories in cities such as New Orleans, La. Further, private well owners rarely get their well water tested due to the presence of a septic system nearby, creating situations where contaminated water may be consumed. Additionally, storm water during heavy rains may cause problems for waste water treatment and contaminate sourced drinking water.

Providing a faster, more accurate and efficient real-time water analysis system is critical because water is the most important resource for human survival, particularly clean water for consumption. Knowing water is contaminated before being consumed is vitally important for preventing outbreaks, epidemics, illnesses and deaths. The most common contaminants in water include microorganisms, nitrate, and arsenic. These contaminants may cause serious illness, and in some circumstances, death. Infants, children, the elderly, and other people with immune deficiencies are particularly susceptible to serious health effects from consuming drinking water with contaminants.

For example, bacteria, viruses, and protozoa (such as *Giardia lamblia* and *Cryptosporidium*) are drinking water contaminants that may rapidly cause widespread and serious illnesses. These microbes primarily come from human or animal wastes that wash into lakes and rivers or that may be carried into shallow groundwater aquifers by rain or irrigation water. Water systems that treat water from reservoirs or rivers before distributing it as drinking water rarely involve microbiological contamination. However, water systems that use groundwater from shallow aquifers are generally required to first chlorinate (disinfect) the water because the aquifers may be susceptible to contamination. Water systems test for the presence of total coliform and E. coli, two kinds of bacteria that signal the presence of human or animal wastes. When these bacteria are found in a water sample, the water supplier must immediately conduct further testing, look for the source of contamination, and in some cases, increase water treatment. If the problem appears serious, the water supplier must inform all customers about the problem and instruct them to use bottled water or boil their tap water before they drink it.

Embodiments of the present disclosure relate generally to systems, apparatuses, and methods for fluid analysis, and in exemplary though non-limiting embodiments, to systems, apparatuses, and methods for real-time online equipment fluid analysis and monitoring.

Embodiments of the present disclosure may be used to determine the status and/or properties of a fluid at any time and at any location as needed to fit a user's needs. Embodiments provide for a real-time fluid analysis system including a sampling system and an analytical system connected to the sampling system. A fluid may be routed through the sampling system and real-time data may be collected from the fluid. The sampling system may process and transmit the real-time data to the analytical system. The analytical system may include a command and control system configured to receive and store the real-time data in a database, and compare the real-time data to existing data for the fluid in the database to identify conditions in the fluid.

Embodiments of the present disclosure provide for a real-time online equipment fluid analysis and monitoring system with cloud based data logging, offering a state-of-the-art, cost efficient fluid monitoring solution that may reduce operating costs at the point of service delivery, provide a proactive preventative maintenance program to minimize equipment downtime, extend equipment life, generate higher resale value on used equipment, and significantly reduce the negative environmental impact compared to existing fluid analysis systems.

Referring to FIG. 1, a real-time fluid analysis system (100) is shown. Fluid analysis system (100) may include an enclosure (300) having a cooling system (302) attached/coupled to a sampling system (304), and an analytical system (400) connected to the sampling system (304). Fluid may be routed out from a fluid source (200) and into cooling system (302) (shown via arrow, A) for cooling the fluid prior to routing the fluid into sampling system (304) (shown via arrow, A) for collecting real-time data from the fluid. In an exemplary embodiment, real-time data may include a "fingerprint" of a fluid sample obtained via spectroscopy. However, other forms of real-time data/information may be obtained from the fluid sample. Sampling system (304) may then process and transmit the real-time data to the analytical system (400) through, for example, an uplink to a WAN (Wide Area Network)/encrypted connection via for e.g., cellular, satellite, Wi-Fi, Bluetooth, and/or Ethernet (RJ-45) connections. Analytical system (400) may be located in the cloud and/or an external storage device. In an example embodiment, external storage device (400a) may be located onboard a ship or other remote structure. A user may access and/or modify the analytical system (400) via for e.g. a web application (HTTP/HTTPS) in a computing device (desktop computer, portable device, etc.) (400a) through any type of encrypted connection described herein. Once processing is complete, fluid may be returned from sampling system (304) to cooling system (302) (shown via arrow, B) and eventually back to fluid source (200) (shown via arrow, B). In other embodiments, if the fluid does not require cooling, fluid may be routed directly from fluid source (200) into sampling system (304) and back.

Analytical system (400) may include a command and control system (406) configured to receive and store the real-time data from the fluid in a database (402), and compare the real-time data to existing data for the fluid in the database (402) to identify conditions in the fluid. See FIG. 1. Particularly, the command and control system (406) may be a hosted software system that may receive the submitted sample of the fluid and process it through a set of existing neural network models for predictive analysis of properties and conditions of the fluid. The neural network models may be configured to target any type of fluid to be analyzed. The resulting output of the sample analysis may be dependent on the fluid submitted, the networks processed, and the statistical percentage accuracy of the given neural network model. In various embodiments, a user may update the existing neural network models or build new neural network models (via "training") if the real-time data does not correspond to any of the set of existing neural network models. In particular embodiments, command and control system (406) may then deploy the updated and/or new neural network models back to the fluid analysis system (100), including the sampling system (304). In various embodiments, command and control system (406) may also be configured to manage a user/client's security and customized settings.

Database (402) may be located in the cloud or in any other type of external storage device. Database (402) may be used to collect and store real-time data relating to different types of fluids (including types of oil and water) and their conditions. Fluids may include but are not limited to any type of industrial fluids or liquids, such as coolants, waste water, etc. Oils may include any type of oil, including but not limited to very light oils such as jet fuels and gasoline, light oils such as diesel, No. 2 fuel oil, and light crudes, medium oils such as most crude oils, and heavy oils such as heavy crude oils, No. 6 fuel oil, and Bunker C. The different "conditions" of oil samples may include but are not limited to wear metals, additives, viscosity, water, TAN, TBN, and particle counts. In exemplary embodiments, the existing real-time data in database (402) may include "fingerprint" information containing the molecular content or makeup of different types of fluid.

In some embodiments, base fluid sensor dashboards may also be provided for each site at time of installation of system (100). Each approved user may have the ability to customize or alter these dashboards as desired. In exemplary embodiments, software in the dashboards may provide real-time monitoring and graphical updates at an update rate not to exceed 180 seconds or at a data change occurrence. Real-time display inclusive of graphical depictions may be capable of continuous updates while data is being viewed. All data screens and access capabilities may be automatically resized to fit the viewing area of the device used to access the dashboards. Data acquisition and analytics in the dashboards may include but is not limited to the following capabilities: analytical comparatives and real-time updates (between sampling system (304) and analytical system (400)); predictive oil changing comparative analysis, chronograph data, financial comparative data; data regarding wear metals, particulate counts, viscosity, TAN, TBN, Nitration, Sulfation, Foreign Oils, Solvents, Glycol, Soot, Dissolved Gases, and/or Oil Additive Depletion (Zn, Mo, Ph, Ca, Mg, Ba, Na), area plots (illustrating how a customer may view a layout of the system (100)); and notifications of pending servicing required.

In particular embodiments, enclosure (300) may be a ruggedized and water-resistant case. For example, enclosure (300) may be mounted via screws and/or bolts onto a flat surface using for e.g. rubber bushings/shock absorbers to minimize vibrational noise. However, enclosure (300) may include other suitable configurations for securely holding both cooling system (302) and sampling system (304).

Embodiments of the present disclosure may be designed using a "plug and play" philosophy. Each component of fluid analysis system (100) may be easily plugged/snapped to other components of fluid analysis system (100) via connectors (306a to 306d) and a wiring harness C. See FIG. 1. For example, cooling system (302) may or may not be plugged into sampling system (304) depending on the temperature of the fluid. In exemplary embodiments, connectors (306a to 306d) may be Eaton STC® "snap" connectors allowing for fluid to be routed into and out of sampling system (304) from cooling system (302).

Figure 2:
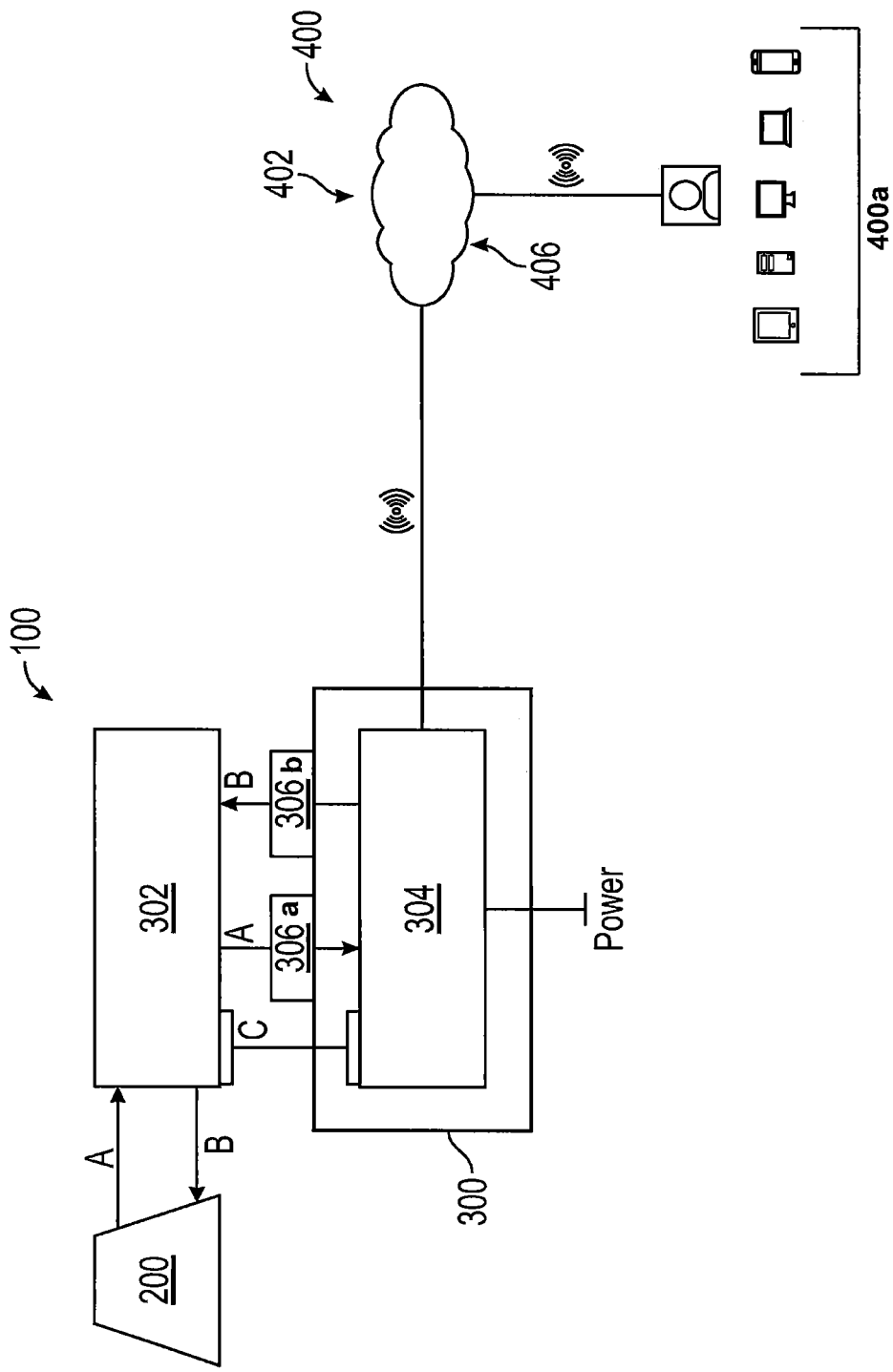
FIG. 2 is a schematic of a fluid analysis system, according to an exemplary embodiment of the present disclosure.

Referring to FIG. 2, an alternative embodiment of fluid analysis system (100) is shown having substantially the same features as fluid analysis system (100) shown in FIG. 1. In this embodiment, cooling system (302) may be installed separate from and/or external to enclosure (300) of fluid analysis system (100) having sampling system (304). Cooling system (302) may be coupled to enclosure (300)/sampling system (304) via connectors (306a, 306b) and wiring harness, C. This particular configuration provides for greater flexibility by allowing for the fluid analysis system (100) to be deployed with or without a cooling system (302) as needed to fit a user's needs. In an exemplary embodiment, cooling system (302) may only be coupled to the enclosure (300)/sampling system (304) if the fluid being routed through the system (100) requires cooling. In this embodiment, enclosure (300) having sampling system (304) may include a smaller sized case than the embodiment of enclosure (300) having both cooling system (302) and sampling system (304) shown in FIG. 1.

Figure 3:
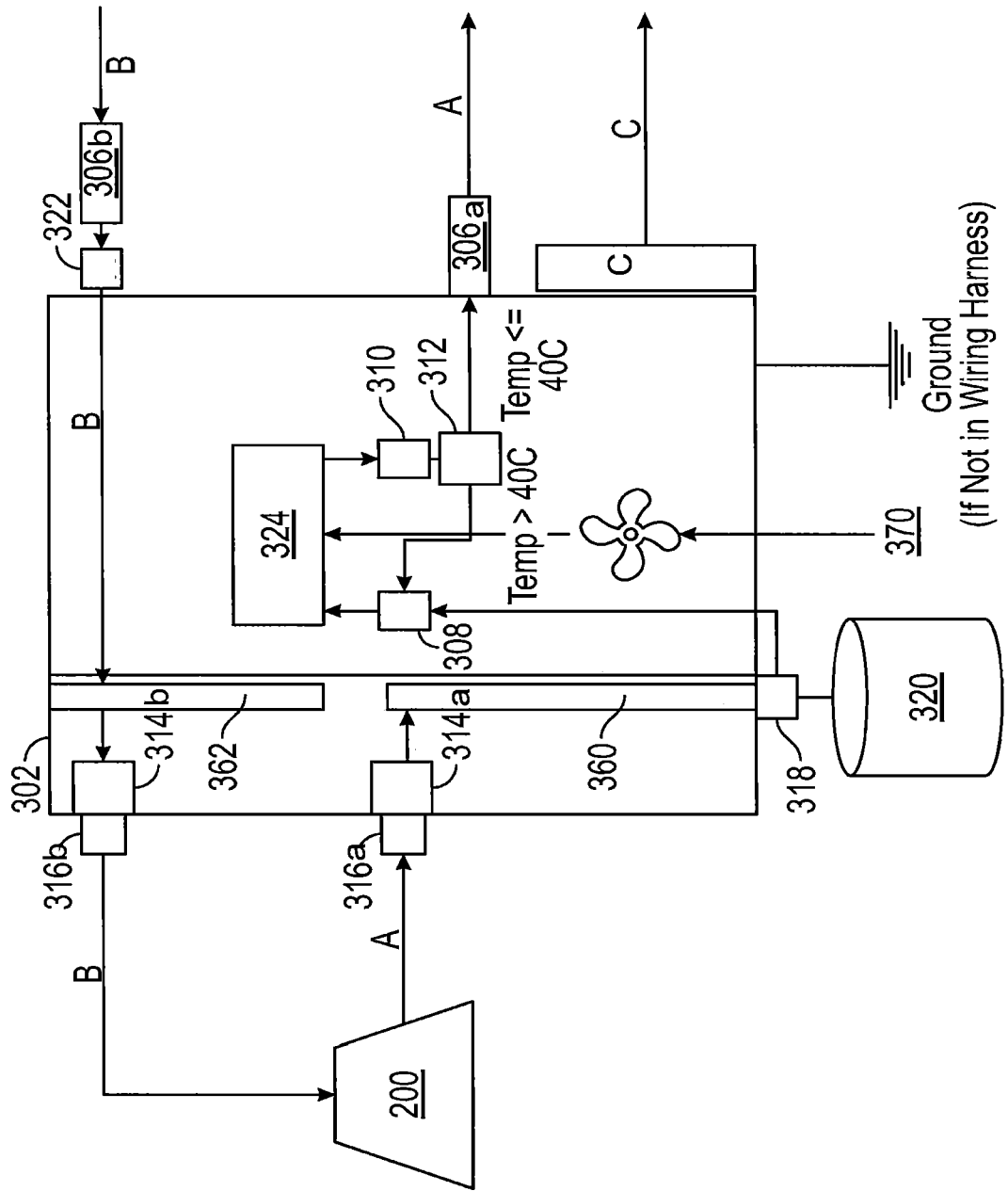
FIG. 3 is a schematic of a cooling system, according to an exemplary embodiment of the present disclosure.

FIG. 3 is a schematic of an exemplary embodiment of cooling system (302). As described herein, cooling system (302) may be a separately pluggable piece that may be coupled to sampling system (304) if and when a fluid requires cooling, or may come pre-installed within an enclosure (300) along with sampling system (304).

Cooling system (302) may be used to control, filter, and cool fluid (for e.g. oil, water, etc.) to be sampled from a fluid source (200). In an exemplary embodiment, fluid may be oil that is routed from an oil source such as an engine (200) via pressure from the engine (200) into cooling system (302) (shown via arrow, A). Fitting (316a) may be used to connect an oil line from a high pressure line from the engine (200) to cooling system (302). In some embodiments, fittings (316a and 316b) may be connectors (306) such as an Eaton STC® "snap" connector. In other embodiments, fittings (316a and 316b) may be ½" FIP fittings. Cooling system (302) may include a valve (314a) connected to source valve manifold assembly (360) and wiring harness, C. Valve (314a) may be used to control when the oil may be allowed into the cooling system (302). In some embodiments, valve (314a) may be an electromechanical single direction solenoid valve. In an exemplary embodiment, valve (314a) may be the AS Series Valve offered by Gems™ Sensors & Controls. Source manifold assembly (360) may be the Manifold Assemblies offered by Gems™ Sensors & Controls. Valve (314a) may be controlled via connections to a controller located in the cooling system (302) and/or located in sampling system (304), which controller may send a signal to the valve (314a) to open and close as needed to allow oil into the cooling system (302).

In various embodiments, oil may first be routed through a filter connection (318) and into a filter (320) located outside cooling system (302). See FIG. 3. In other embodiments, filter (320) may be located inside cooling system (302). Filter connection (318) and filter (320) may be used to prevent for e.g. debris in oil from entering cooling system (302) and damaging cooling system (302) and eventually sampling system (304). Oil may then be routed into a pressure reducer (regulator) valve with a pressure sensor (308). Pressure reducer valve (308) may include two inputs and one output. See FIG. 3. In an exemplary embodiment, pressure reducer valve (308) may be the BB-3 series stainless steel back-pressure regulator offered by Tescom™. In various embodiments, pressure reducer valve (308) may reduce the pressure from dangerously high pressures (>50 psi) in an engine (200) to between approximately 1 and 50 psi (depending on fluid type). Once the oil is reduced to a safe pressure level, oil may be routed into a cooler/radiator (324) and then to a temperature sensor (310) and a 2-way solenoid valve (312). In some embodiments, cooler (324) may either be a simple radiant heat sink or a fluid cooler system. In an exemplary embodiment, cooler (324) may be the MMOC-10 Universal 10-Row Oil Cooler offered by Mishimoto™.

In an exemplary embodiment, if the temperature sensor (310) detects that the oil is at a temperature </=40° C., it may switch valve (312) and route the oil out of cooling system (302) and into sampling system (304) (shown via arrow, A). See FIG. 3. However, if the temperature sensor (310) detects that the oil is at a temperature >40° C., it may route the oil back into pressure reducer valve (308) and into cooler (324) via valve (312) until the oil reaches the desired temperature (for e.g. 40° C.). This temperature is relevant because it is related to measuring the oil's viscosity. A lubricating oil's viscosity may be measured either based on its kinematic viscosity or its absolute (dynamic) viscosity. An oil's kinematic viscosity is defined as its resistance to flow and shear due to gravity at a given temperature. However, simply stating an oil's viscosity is meaningless unless the temperature at which the viscosity was measured is defined. For most industrial oils, it is common to measure kinematic viscosity at 40° C. because this is the basis for the ISO viscosity grading system (ISO 3448). In various embodiments, fan (370) may be installed within cooling system (302) and turned on as needed (for e.g. if the temperature of the oil is >40° C.) to assist cooler (324) in cooling the oil based on the temperature of the fluid and radiant air temperature. See FIG. 3. Fan (370) may be controlled via the controller described herein in sampling system (304) (e.g., see controller (332) shown in FIG. 7) and/or cooling system (302) (not shown).

Wiring harness, C, may be used to connect various connections of cooling system (302) described herein to sampling system (304). See FIG. 3. Once the oil is adequately sampled by sampling system (304), oil may be routed back from sampling system (304) to cooling system (302) (shown via arrow, B in FIGS. 1 and 2). To facilitate this return, cooling system (302) may include an air valve (322) that may be opened as needed to allow air to purge the line and speed up the return of oil if there is no pressure to push/drain the oil back into cooling system (302) from sampling system (304). Oil may then be routed out of cooling system (302) and back to engine (200) via a similar fitting (316b)-valve (314b)-return valve manifold assembly (362) connection as described herein for entry of oil into cooling system (302). See FIG. 3. Return manifold assembly (362) may be the Manifold Assemblies offered by Gems™ Sensors & Controls.

Figure 4:
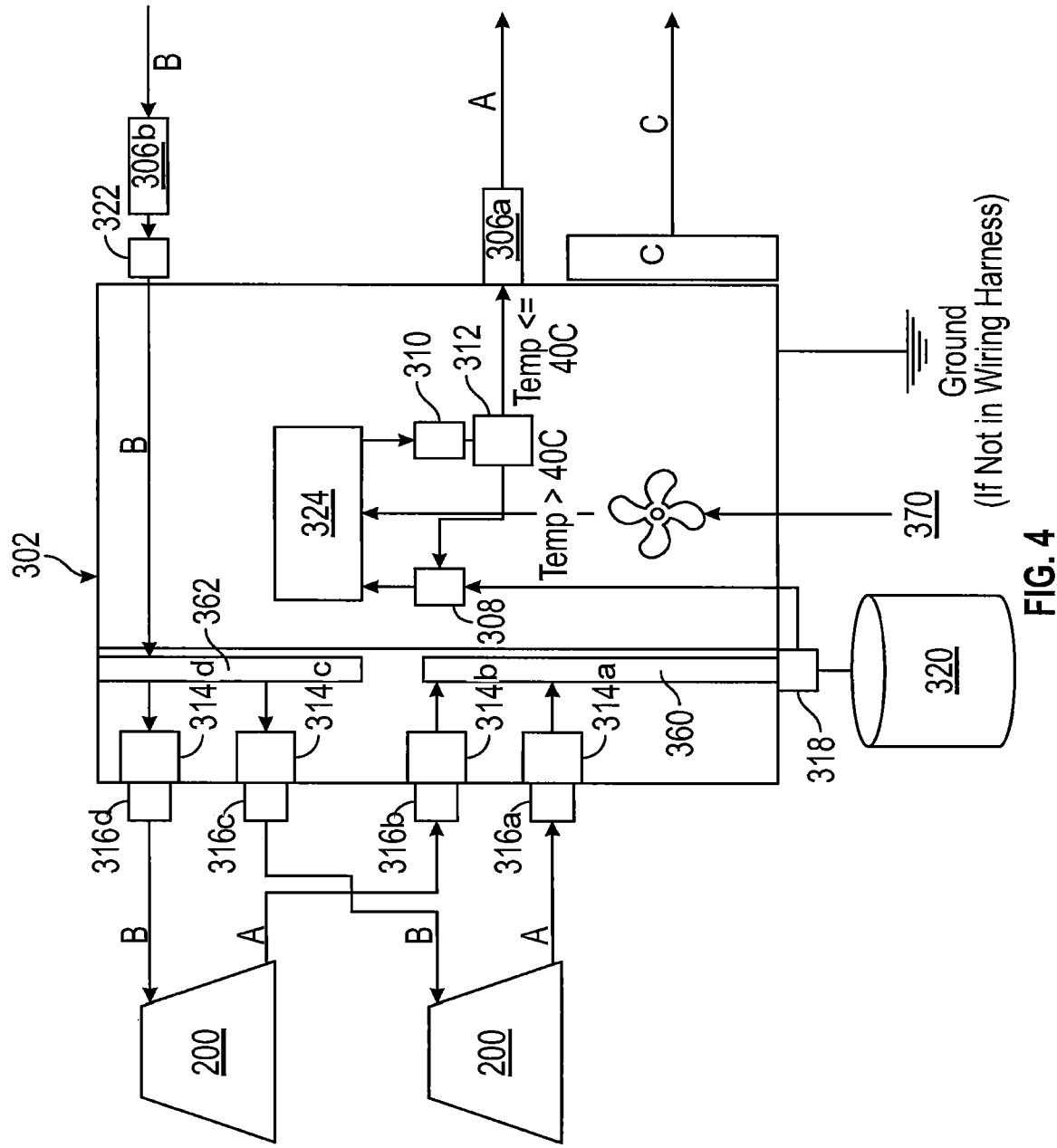
FIG. 4 is a schematic of a cooling system, according to an exemplary embodiment of the present disclosure.

Referring to FIG. 4, an alternative embodiment of cooling system (302) is shown having substantially the same features as cooling system (302) shown in FIG. 3. In this embodiment, cooling system (302) is shown as having connections to multiple fluid sources (200) for cooling and routing fluid into sampling system (304). In a particular embodiment, fluid from only one fluid source may be cooled and sampled at a time. In an exemplary embodiment, cooling system (302) may be simultaneously connected to two engines (200), with multiple fittings (316a to 316d) and valves (314a to 314d) attached to each of the input/inlet and return/outlet sides, each of which may be controlled independently based on the oil to be sampled. As shown, valves (314a to 314d) connected to each of the two engines (200) may be connected to one source manifold assembly (360) and one return manifold assembly (362). Each valve (314a to 314d) may be controlled via connections to a controller located in the cooling system (302) (not shown) and/or located in sampling system (304) (e.g., controller (332) shown in FIG. 7), which controller may send a signal to an appropriate valve (314a to 314d) on the source and/or return manifold assemblies (360, 362) to open to allow flow of oil, while closing other valves (314a to 314d) depending on the sample and/or engine (200) selected for sampling.

Figure 5:
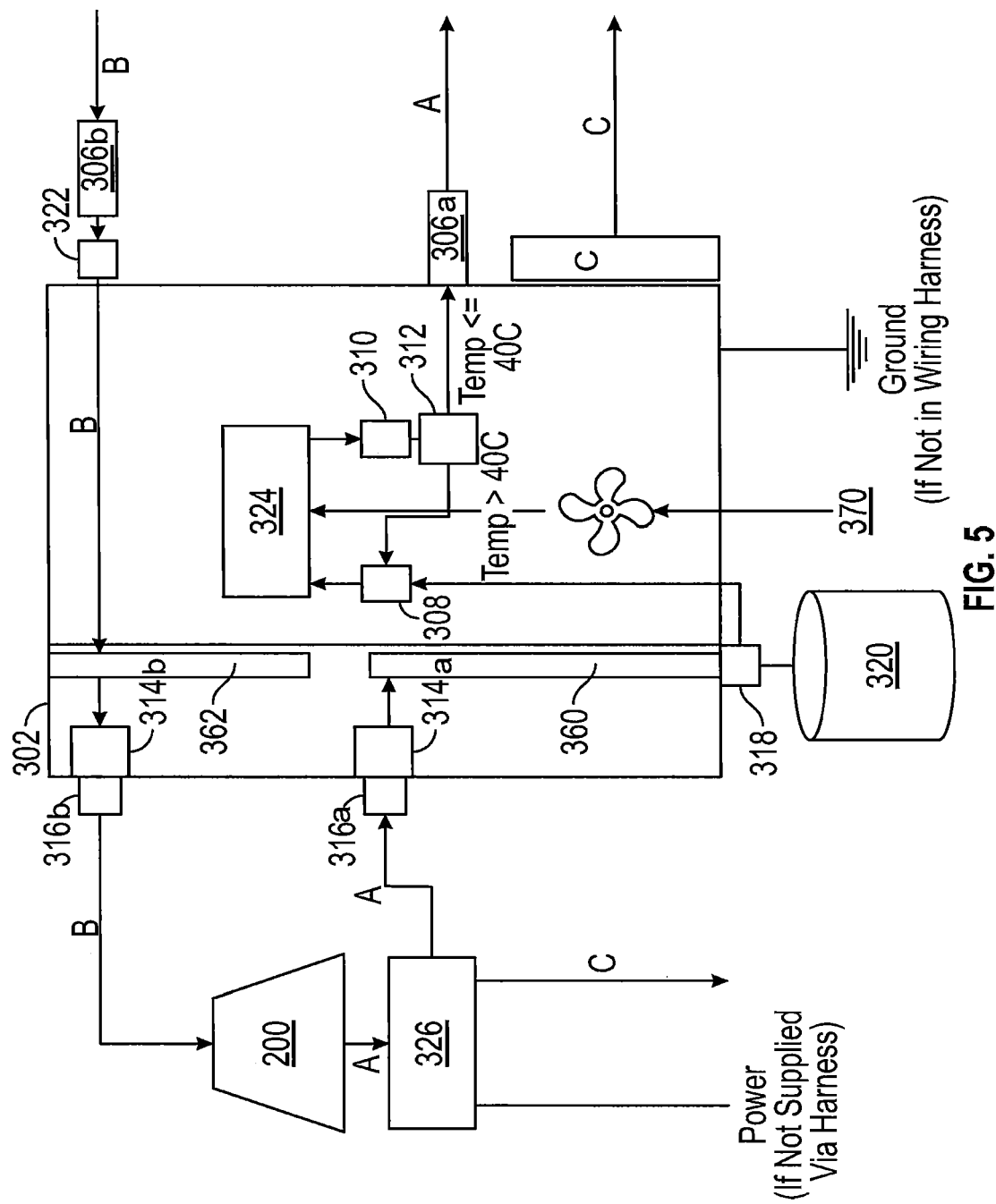
FIG. 5 is a schematic of a cooling system, according to an exemplary embodiment of the present disclosure.

FIG. 5 is a schematic of an alternative embodiment of cooling system (302) having substantially the same features as cooling systems (302) shown in FIGS. 3 and 4. In this embodiment, cooling system (302) may include a pump (326) connected to a fluid source (200) with fluids having low/no pressure. Pump (326) may provide additional pressure/movement for these fluids to be routed into cooling system (302) and eventually into sampling system (304) (e.g., see FIGS. 1 and 2). In an exemplary embodiment, oil may be routed from engine (200) into pump (326), which pump (326) may then pump oil into cooling system (302) (shown via arrow, A). Oil may first be routed into filter connection (318)/oil filter (320), pressure reducer valve (308), cooler (324), temperature sensor (310), 2-way solenoid valve (312), sampling system (304) (e.g., see FIGS. 1 and 2), and back to cooling system (302) and engine (200) as described herein. Pump (326) may include connections via wiring harness, C, to sampling system (304). Pump (326) may be initialized via connections to a controller located in the cooling system (302) (not shown) and/or located in sampling system (304) (e.g., see controller (332) shown in FIG. 7) when a fluid sample is requested. In various embodiments, controller in cooling system (302) and/or sampling system (304) (e.g., see controller (332) shown in FIG. 7) may shut pump (326) down once sampling is complete, then open air valve (322) as needed to allow air to purge the line and speed up the return of oil if there is no pressure to push/drain the oil back into cooling system (302).

Figure 6:
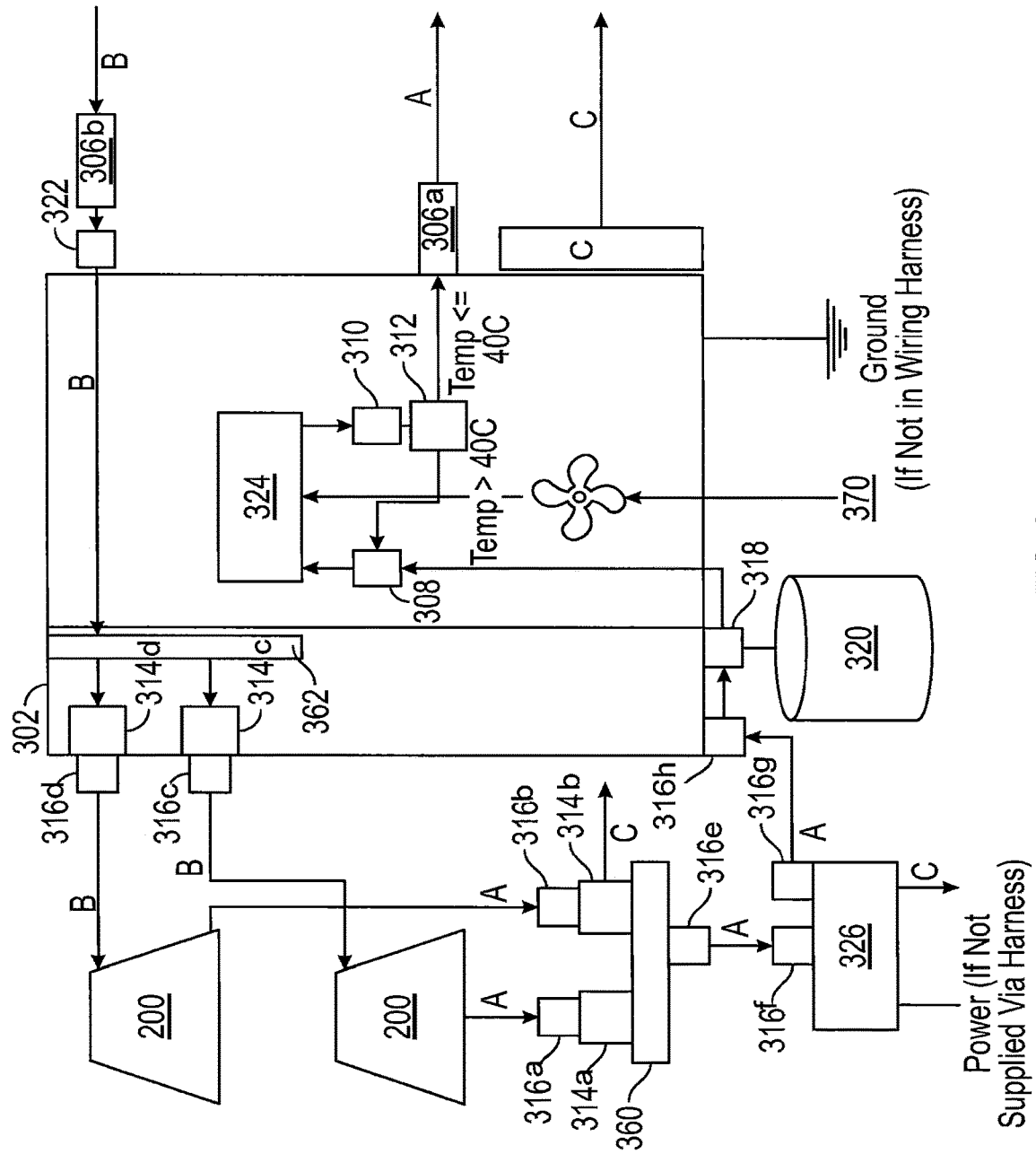
FIG. 6 is a schematic of a cooling system, according to an exemplary embodiment of the present disclosure.

FIG. 6 is a schematic of an alternative embodiment of cooling system (302) having substantially the same features as cooling systems (302) shown in FIGS. 3, 4, and 5. In this embodiment, cooling system (302) may include a pump (326) connected to multiple fluid sources (200) with fluids having low/no pressure. As shown, source valve manifold (360) may be located external to cooling system (302), thereby preventing duplicative valve (314a to 314d) systems on the input line to cooling system (302). Further, providing the source valve manifold (360) external to cooling system (302) allows for oil from multiple engines (200) to be sourced into a single line prior to being routed into pump (326), thus eliminating the need for multiple pumps (326). See FIG. 6. As shown, oil may be routed from the two engines (200) into fittings (316a and 316b) and valves (314a and 314b) attached to a source valve manifold (360). Each valve (314a to 314d) may be controlled via connections to a controller located in the cooling system (302) (not shown) and/or located in sampling system (304) (e.g., see controller (332) see FIG. 7), which controller may send a signal to an appropriate valve (314a to 314d) on the source and/or return manifold assemblies (360, 362) to open to allow flow of oil, while closing the other valve (314a and/or 314b) depending on the sample and/or engine (200) selected for sampling. Once a valve (314a to 314d) is opened, oil may be routed into pump (326), and subsequently pumped into cooling system (302), including the filter connection (318)/oil filter (320), pressure reducer valve (308), cooler (324), temperature sensor (310), 2-way solenoid valve (312), sampling system (304), and back to cooling system (302) and engine (200) as described herein.

Figure 7:
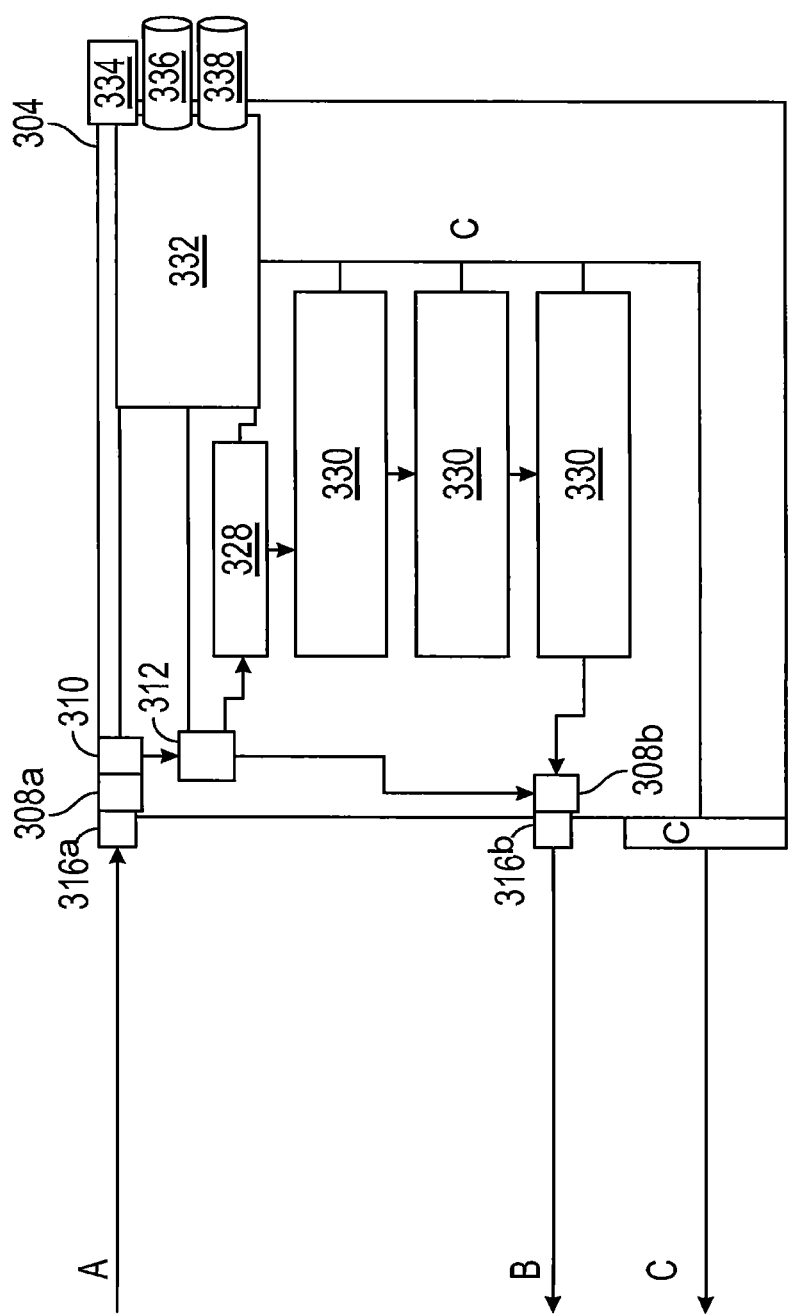
FIG. 7 is a schematic of a sampling system, according to an exemplary embodiment of the present disclosure.

Referring to FIG. 7, a sampling system (304) is shown. As shown, arrow A represents fluid being routed in from cooling system (302) and/or fluid source (200), arrow B represents fluid being returned back to cooling system (302) and/or fluid source (200) after sampling, and arrow C represents wiring harness connectors between components of sampling system (304) and between sampling system (304) and cooling system (302).

Sampling system (304) may include at least one removable and replaceable sub-sampling system (330). Particularly, sampling system (304) may include an "assembly line" of multiple daisy-chained sub-sampling systems (330) via for e.g. a wiring harness, C. In various embodiments, multiple sub-sampling systems (330) may be stacked on top of each other and "snap" connected together via for e.g. connectors (306) (e.g., see FIGS. 1 to 6). See FIG. 7. In particular embodiments, connectors (306) may be the Eaton STC® "snap" connectors allowing for fluid to be routed into and out of sub-sampling systems (330). In this embodiment, each sub-sampling system (330) may have a female input connector (on the top) and a male output connector (on the bottom), allowing each sub-sampling system (330) to be stacked sequentially to satisfy fluid and target requirements. The types of sub-sampling system (330) used for sampling system (304) may be dependent on the fluid and targeted identification criteria needed.

In various embodiments, sampling system (304) may further include connections between input and output fittings (316a and 316b), input and output pressure reducer valves with pressure sensors/transducers (308a and 308b), input temperature sensors (310), at least one viscometer (328), a 2-way solenoid valve (312), and at least one controller (332). Particularly, sampling system (304) may include several wiring harness connectors, C, that connect from the at least one controller (332) to each sub-sampling system (330) (via for e.g. dovetails for coupling), the at least one viscometer (328), the pressure reducer valves with pressure sensors/transducers (308a and 308b), temperature sensors (310), 2-way solenoid valve (312), and a ribbon to the external connector for the cooling system (302) (e.g., see FIGS. 1 to 6). Controller (332) may control the sampling system (304) and/or cooling system (302) and interact with analytical system (400) by for e.g. submitting real-time data obtained from fluids being sampled to analytical system (400).

Once fluid is routed into sampling system (304), bypass valve (312) may divert the fluid back to cooling system (302) via a return line if the pressure and/or temperature of the fluid are too high or low. Pressure sensor/transducer (308a and 308b) may be located at the output/return line to perform a pressure comparison between the input and output pressures of the fluid to determine if a significant enough drop exists to identify the presence of a leak. This may be accomplished during sampling of the fluids by letting the sub-sampling systems (330) equalize in pressure while the samples are being taken. A change in pressure after equalization, i.e. a drop, may infer the presence of a leak within the sub-sampling systems (330) or at the output valve (308a and 308b). To determine if the output valve (308a and 308b) is leaking, a user may monitor the current required to operate the solenoid. As valves driven by solenoids begin to fail, they will draw more current to perform the same functions (i.e. sticky valve, a short, etc.). Current monitoring on the solenoid valve lines may constitute another part of self-diagnostics for sampling system (304)/fluid analysis system (100).

As shown, bypass valve (312) may divert the fluid to the at least one viscometer (328) if the pressure and/or temperature of the fluid are at an appropriate level. At least one viscometer (328) may be used to measure the viscosity and flow parameters of the fluid. In an exemplary embodiment, viscometer may be the VISCOpro 2000 Process Viscometer offered by the Petroleum Analyzer Company, L.P. d/b/a PAC. Once the viscosity of the fluid is measured, fluid may be routed into the at least one sub-sampling system (330). In an exemplary embodiment, fluid may be routed from the at least one viscometer (328) into three sub-sampling systems (330) stacked on top of other, the fluid being sampled while in each sub-sampling system (330). See FIG. 7.

All components of sampling system (304) may be connected to controller (332) via wiring harness connectors, C. See FIG. 7. In an exemplary embodiment, controller (332) may be an ARM (Acorn RISC Machine/Advanced RISC Machine) based system with a custom shield for connecting to cooling system (302), sub-sampling systems (330), and/or other components of cooling and sampling systems (302, 304) (e.g., see FIGS. 1 to 7). In exemplary embodiments, controller (332) may include an RJ45 (CATS/6) Ethernet connection (334), an SMA (SubMiniature version A) connection (336) for an antenna or an antenna dongle, and a power connector (338). Controller (332) may also include connections including for e.g. USB, HDMI, and Bluetooth connections, and may be powered via a Mini-USB connection. In exemplary embodiments, controller may be the Raspberry Pi 3 Model B, Raspberry Pi Zero, or Raspberry Pi 1 Model A+. In other embodiments, controller (332) may be the Mojo Board V3 offered by Embedded Micro—an FPGA (Field Programmable Gate Array) with multiple pre-made shields. Shields used to connect controller (332) to other components of sampling system (304) and/or cooling system (302) (e.g., see FIGS. 1 to 6) may include the Servo Shield (used for connecting to servos/solenoids on valves), Proto Shield (used for prototyping), IO Shield (used for displaying output, buttons for input, and switches for configuration options), and/or stackable headers (used to stack shields) offered by Embedded Micro. In some embodiments, controller (332) may be placed within its own enclosure separate from enclosure (300) of sampling system (304) to protect controller (332) in case of a catastrophic fluid failure/leak within sampling system (304). In other embodiments, controller (332) may also be included in cooling system (302).

In exemplary embodiments, controller (332) may include its own customized software to assist sampling system (304) in performing analysis of fluid and sending/receiving real-time data regarding the fluid to analytical system (400). In various embodiments, software of controller (332) may include information including but not limited to communication protocols, security settings, sampling system (304) interaction, cooling system (302) sub-controller/controller, temperature and pressure sensors in system (100), as well as information pertaining to the determination in a spectroscopy based sub-sampling system (330) regarding how to trigger an excitation system and read outputs from the source from a detection system connected to the source. An exemplary embodiment of this software will be described in further detail in the discussion relating to the flowchart of sampling system (304) shown in FIG. 17. In some embodiments, this software of sampling system (304) may also monitor the system (100) for leaks and other potential problems.

In a particular embodiment, an onboard sampling system (304) may poll the analytical system (400) in the cloud every pre-determined number of minutes for specific commands/instructions. When a sampling system (304) is deployed, its inbuilt software may be pre-keyed with a custom login/password and/or entered by a user onboard. Upon startup, that login/password may retrieve the configuration settings for that sampling system (304), which settings may contain settings entered into the sampling system (304) and any other information that the onboard system (100) can detect from its own hardware. An example setting may be the sampling schedule and retention period of the fluid to be sampled. With a limited amount of onboard space available for storing sample data, if the onboard system (100)/sampling system (304) is expected to be in a remote area/out of contact for an extended period of time and begins to fill its storage with automated samples, it may then have to start dropping samples. Upon establishing a connection to the analytical system (400) in the cloud, the onboard system (100)/sampling system (304) may then proceed to upload all the automated sample data it previously stored when disconnected from the internet.

Figure 8:
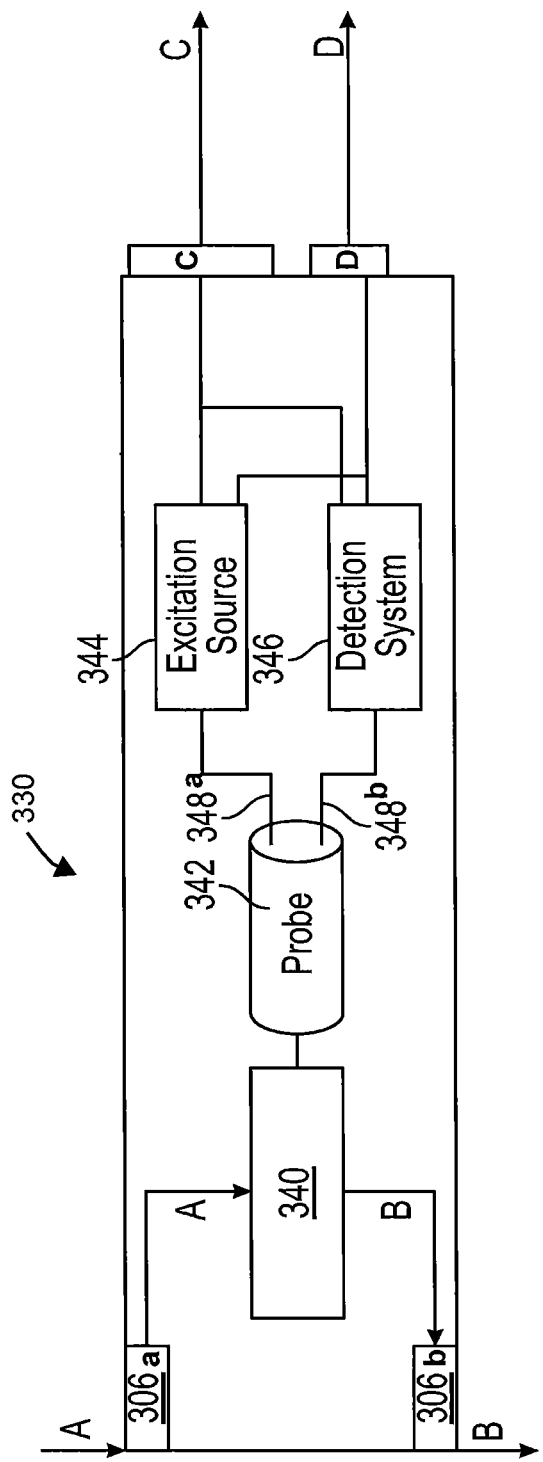
FIG. 8 is a schematic of a sub-sampling system, according to an exemplary embodiment of the present disclosure.

Referring to FIG. 8, a sub-sampling system (330) is shown. Sub-sampling system (330) may be a removable and replaceable component/system that may be plugged in to sampling system (304) (e.g., see FIG. 7) as necessary to perform specific types of analysis on a sample of fluid being routed through sampling system (304) and obtain real-time/ "fingerprint" information regarding the fluid sample. Combining multiple sub-sampling systems (330) by simply "plugging" multiple sub-sampling systems (330) together during assembly of the sampling system (304) may allow for many different types of fluid samples to be analyzed, and many different characteristics of those samples to be obtained.

In exemplary embodiments, accurate analysis may be performed and precise data obtained from fluid samples by performing electro-optical analysis on the fluids. Sub-sampling system (330) may utilize a spectral scanner/spectrometer/custom electro-optical system to instantaneously and continuously scan and inform a user of the molecular makeup and condition of any fluids such as for e.g. industrial oil and water. Different types of fluids/materials have their own "fingerprint" and the electro-optical system may read and analyze the differences between these materials. In exemplary embodiments, sub-sampling system (330) may be at least one of a Raman sub-sampling system (330, 350) (e.g., see FIG. 9), a fluorescence sub-sampling system (330, 352) (e.g., see FIG. 10), an absorbance sub-sampling system (330, 354) (e.g., see FIG. 11), a Fourier Transform IR absorbance sub-sampling system (330, 356) (e.g., see FIG. 12), and an absorbance-fluorescence-scatter sub-sampling system (330, 358) (e.g., see FIG. 13). Each type of electro-optical analysis based sub-sampling system (330) may provide for different methods of analyzing the fluids by identifying different parts of the fluids.

In exemplary embodiments, sub-sampling system (330) (e.g., see FIG. 8) may include connections between pluggable fluid input and output connectors (306a and 306b) (i.e., a female input on top and a male output on the bottom), a continuous-flow or flow-through electro-optical sampling chamber (340) connected to a fiber optic probe (342), and fiber optic cables (348a, 348b) connected to both the probe (342) and each of an excitation source/electromagnetic radiation source (344) and a detection system (346). See FIG. 8. In a particular embodiment, sampling chamber (340) may be a glass, quartz, borosilicate, or polysterene chamber. Sub-sampling system (330) may also include wiring harness connections to controller (332) (e.g., see FIG. 7) described herein (shown as arrow C) and a power wire harness connection/power plug to power components of sub-sampling system (330) (shown as arrow D). Wiring harness connector, C, may connect to the microcontroller (332) and in some embodiments, use a dovetail to inter-connect to various components of fluid analysis system (100) described herein. In an exemplary embodiment, power plug/connection, D, may be connected to a power distribution unit (PDU) inside the enclosure (300)/sampling system (304).

As shown, fluid may be routed in to sub-sampling system (330) from valve (312) and/or at least one viscometer (328) into sampling chamber (340) for analyzing (e.g., see FIG. 7). Particularly, controller (332) may flush a sample of the fluid through the chamber (340) for a certain time depending on the distance between sampling system (304) and fluid source (200) in order to remove previous fluid from other sources (200) and to ensure a clean sample. Controller (332) may then close relevant input and output valves (308a and 308b) in sampling system (304) (e.g., see FIG. 7) and/or valves (314a to 314d) in cooling system (302) (e.g., see FIGS. 3 to 6) to stop fluid flow. Controller (332) may then be used in conjunction with probe (342), excitation source (344), and detection system (346) to obtain real-time data/fingerprint information regarding the fluid (e.g., see FIG. 8). Particularly, controller (332) may begin collecting samples by triggering the excitation source (344) and simultaneously reading the resulting fluid real-time data from the detection system (346). The still nature of the fluid sample in the sampling chamber (340) may further allow for application of time resolved optical spectroscopy to the fluid. Once adequate sampling has been performed (and relevant real-time data obtained) on fluid samples, fluid may be routed to another sub-sampling system (330) and/or returned back to cooling system (shown via arrow B).

In exemplary embodiments, controller (332) may also, based on learned feedback from the sampling system (304), adjust the focus of the probe (342) by increasing or decreasing the distance of the probe to the sampling chamber (340). While adjusting this distance, controller (332) may continually take samples to try to match a known good focus. The known good focus may be established via samples from the specific fluid in question that may already be stored in database (402) prior to installation of system (100). A focus calibration may be issued manually or automatically during a focus run, or based on a baseline standardization sample. In various embodiments, the focal distance of probe (342) may be adjustable during setup (via commands from microcontroller (332)) so as to obtain the highest resolution samples of the fluid. Particularly, controller (322) may utilize a worm gear or type of dynamic adjuster/glide system controller to adjust the focus of the probe (342).

Excitation source (344) and detection system (346) may be used in tandem to perform fluid analysis (e.g., see FIG. 8). Detection system (346) may act as electro-optical "eyes" for a given excitation source (344). Controller (332) may inform the detection system (346) to prepare for sampling, after which it may inform the excitation source (344) to "fire" electromagnetic radiation into the fluid sample, and the detection system (346) may then register the results of this "firing". In exemplary embodiments, this "firing" may be milliseconds to seconds long depending on the excitation source used and the type of detection required. In particular embodiments, excitation source (344) may be an LED source (specific chromatic source, mono chromatic, UV), IR/NIR (infrared/near-infrared) source, and/or wavelength stabilized laser (specific wavelength laser for excitation). In various embodiments, detection system (346) may be a type of charge-coupled device (CCD) (that may simply report direct data without a spectrometer for filtering), a set of photodiodes with a matching set of spectral filters (looking for specific wavelengths), and/or a spectrometer coupled to a thermally controlled CCD that may detect multiple sources coupled to the spectrometer for filtering.

In some embodiments, sub-sampling systems (330) may be further configured to divert approximately 1 to 10 mL of the fluid samples being analyzed into a retrieval storage compartment/container within sampling system (304). Doing so may allow for the fluid sample to be analyzed via Gas Chromatography/Mass Spectrometry if the analytical system (400) determines that it cannot accurately identify the sample it has been given. In various embodiments, sub-sampling system (330) may include a port wherein the compartment/container containing the fluid sample may be removed and/or shipped to an external location for further processing and analyzing.

Figure 9:
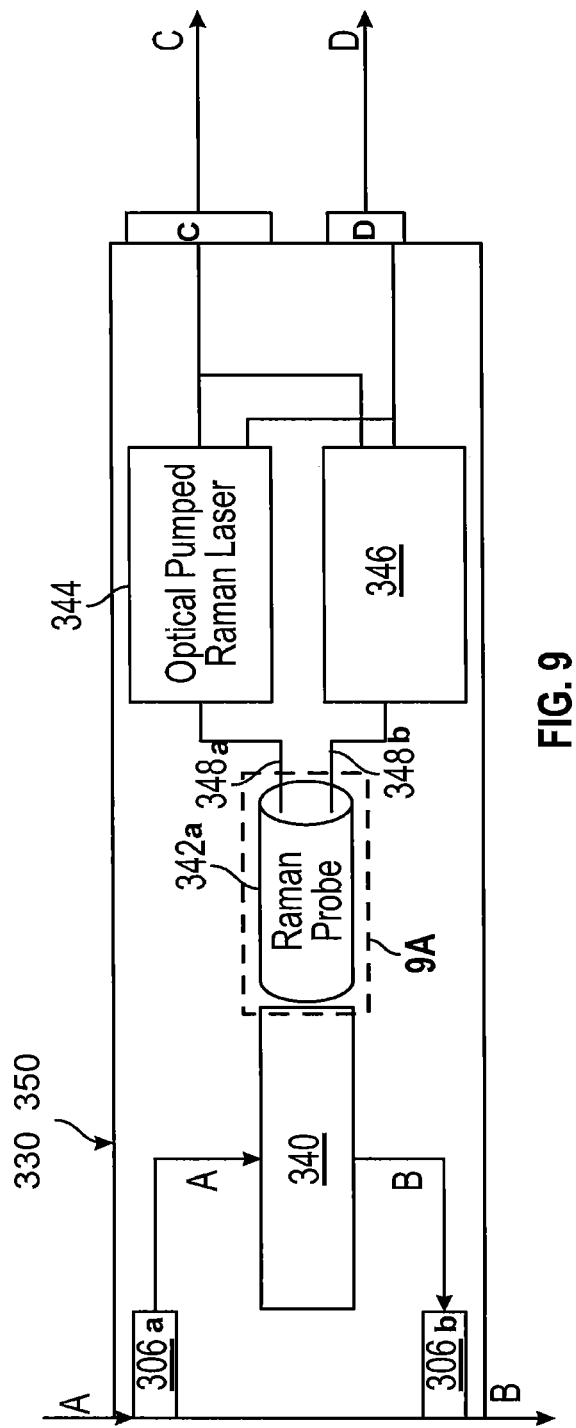
FIG. 9 is a schematic of a Raman sub-sampling system, according to an exemplary embodiment of the present disclosure.
Figure 9A:
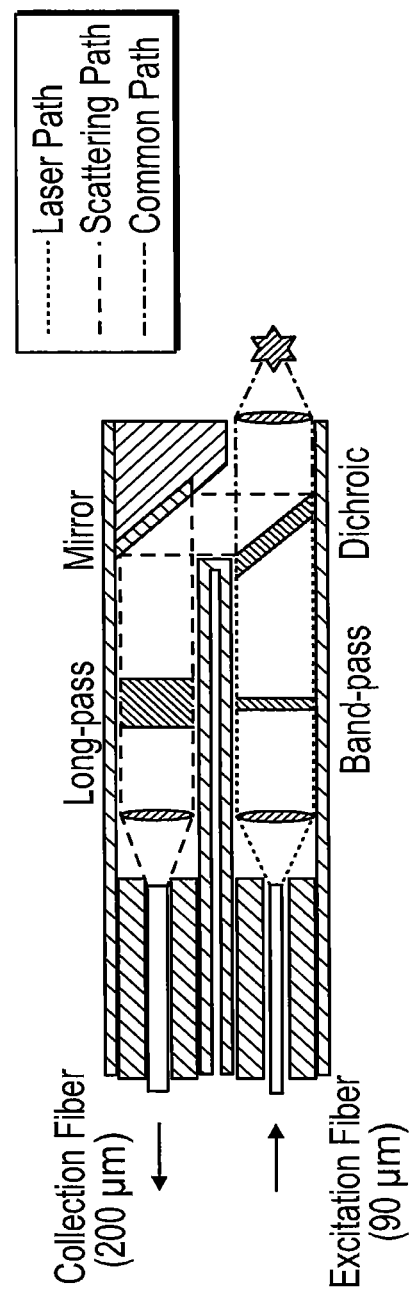
FIG. 9A is an illustration of inner components of a Raman probe, according to an exemplary embodiment of the present disclosure.

Referring to FIG. 9, a Raman sub-sampling system (330, 350) is shown. FIG. 9A is an illustration of inner components of a Raman probe (342). Raman sub-sampling system (330, 350) substantially includes similar features as the sub-sampling system (330) described herein in FIG. 8, with particular modifications made to the type of probe (342a), excitation source (344), and detection system (346).

Raman spectroscopy is a spectroscopic technique for obtaining information about molecular vibrations of a sample that may be used for sample identification and quantitation. The technique involves shining a light source (e.g., laser) on a sample and detecting the scattered light. The majority of the scattered light may be of the same frequency as the excitation source, known as Rayleigh or elastic scattering. A very small amount of the scattered light may be shifted in energy from the laser frequency due to interactions between the incident electromagnetic waves and the vibrational energy levels of the molecules in the sample. Plotting the intensity of this "shifted" light versus frequency results in a Raman spectrum of the sample ("Raman shift"). Generally, Raman spectra are plotted with respect to the laser frequency such that the Rayleigh band lies at 0 cm$^{-1}$. On this scale, the band positions will lie at frequencies that correspond to the energy levels of different functional group vibrations.

In exemplary embodiments, a "fingerprint" of a fluid sample may be obtained from a Raman sub-sampling system (330, 350) via a single frequency wavelength that uses a specialized Raman probe (342a) to capture the "scatter" of molecular energy level changes. In exemplary embodiments, Raman sub-sampling system (330, 350) may include a specialized Raman probe (342a), a stabilized wavelength laser (344), and a set of photo diodes and spectral filters (346) targeting the required wavelengths of a Raman shift. In various embodiments, chamber (340) may be quartz or glass flow-through/continuous flow chamber based on the wavelength and power of the laser (344). For example, if the laser (344) is in the UV range, then chamber (340) may be a quartz chamber. In exemplary embodiments, laser (344) may be a 785 nm wavelength optical pumped Raman laser. In particular embodiments, Raman probe (342a) may be the General Purpose Raman Probes offered by Ocean Optics, Inc.

As shown in FIG. 9A, the excitation EM (electro-magnetic) source may be emitted into excitation fiber and through a band-pass wavelength filter and a dichroic filter of the Raman probe (342a). The reflected EM source may then scatter against the dichroic filter, reflect off a mirror and through a long-pass wavelength filter and collection fiber, and be transported via fiber optic cable (348a) (e.g., see FIG. 9) and collected on the photodiodes (346). Raman probe (342a) may be used to measure the wavelength shift(s) (Raman shift) of the excited sample. These Raman shifts may show up as peaks in a spectral graph. The Raman shifts may be converted to wavelengths via the following formulas:

$$\hat{v} = \frac{10000}{\lambda}$$

$$\hat{v} = \frac{v}{100 \cdot c}$$

$$\hat{v} = \frac{e}{h \cdot c} \cdot \frac{E}{100}$$

Wavenumbers—Wavelength
Wavenumbers—Frequency
Wavenumbers—Electron volt
$\tilde{v}$: Wavenumbers (cm$^{-1}$)
$\lambda$: Wavelength (μm)
$v$: Frequency (s$^{-1}$)
c: Velocity of light (2.99792458·10$^8$ m/s)
e: Elementary charge (1.60217733·10$^{-19}$ C)
h: Planck's constant (6.6260755·10$^{-34}$ J·s)
E: Energy (eV)

In exemplary embodiments, the "fingerprint" of the fluid sample may be obtained by measuring/determining the value of this "Raman shift".

Figure 10:
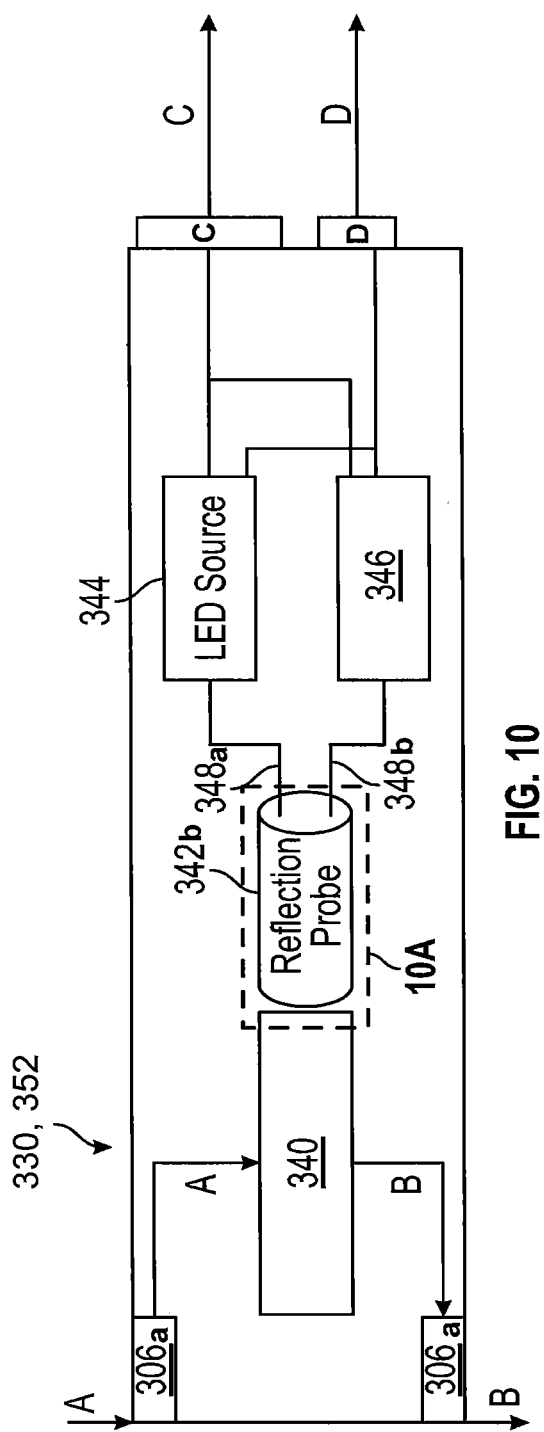
FIG. 10 is a schematic of a fluorescence sub-sampling system, according to an exemplary embodiment of the present disclosure.
Figure 10A:
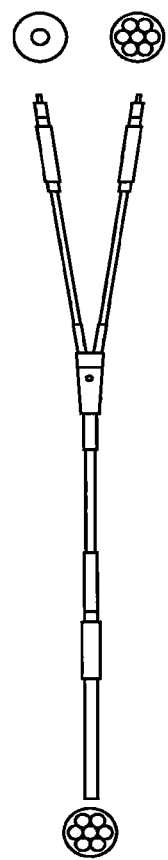
FIG. 10A is an illustration of a reflection probe, according to an exemplary embodiment of the present disclosure.

Referring to FIG. 10, a fluorescence sub-sampling system (330, 352) is shown. FIG. 10A is an illustration of a type of reflection probe (342b) used in fluorescence sub-sampling system (330, 352). Fluorescence sub-sampling system (330, 352) substantially includes similar features as the sub-sampling system (330) described herein in FIG. 8, with particular modifications made to the type of probe (342b), excitation source (344), and detection system (346).

Fluorescence spectroscopy based systems utilize electromagnetic spectroscopy to analyze fluorescence from a sample. These systems may involve using a beam of light, usually ultraviolet light, that excites the electrons in molecules of certain compounds and causes them to emit light; typically, but not necessarily, visible light. Fluorescence sub-sampling/detection systems may generally require at least: an excitation light source, a fluorophore (fluorescent chemical compound that can re-emit light upon light excitation), wavelength filters to isolate emission photons from excitation photons, and a detector that registers emission photons and produces a recordable output, usually as an electrical signal.

A "fingerprint" of a fluid sample may be obtained from a fluorescence sub-sampling system (330, 352) based on the following technology: Using a light source that will shine broadband light (i.e., light in many wavelengths) allows for the ability to emit photons in various energies. When the light source shines on a fluid/oil sample, photons in the light penetrate into the sample, meeting in their way the molecules that compose the sample. Each of the molecules in the sample has its own specific set of energy, and if a photon with a certain energy hits a molecule, the photon may simply disappear. Out of the billions of photons sent by the light source, some of them may disappear—particularly, those with energy that matches the sample's vibrations. After the photons penetrate into the sample and repeatedly hit the sample's molecules, some of the photons may leave the sample. At this point, it is important to "ask" these photons what they have seen, which may be done by analyzing the color of the light that comes out of the sample. Some wavelengths in the light may be missing, or more precisely, some wavelengths in the light may be attenuated relative to the others. These wavelengths are the ones that match the sample's energy vibrations, and therefore constitute the transmission/absorbance/fluorescence "fingerprints" of the sample. Thus, in an exemplary embodiment of the present disclosure, to obtain a "fingerprint" of a sample via fluorescence spectroscopy, a broadband light source may first be shined on a sample. Light coming out of the sample may then be collected and the wavelength content of the light may be analyzed. The molecular content of the sample may then be analyzed and determined by comparing the wavelength of the light that was initially sent/shined on the sample with the wavelength of the light that was collected after leaving the sample.

In exemplary embodiments, fluorescence sub-sampling system (330, 352) may include a reflection probe (342b), an LED source (344) connected to the probe (342b), and a detector (346) connected to the probe (342b) used to measure parameters of fluorescence of the sample, including its intensity and wavelength distribution of emission spectrum after excitation by a certain spectrum of light, which parameters may be used to identify the presence and the amount of specific molecules in the sample. In various embodiments, chamber (340) may be quartz or polystyrene flowthrough cell/continuous flow chamber. For example, if source (344) is a low power LED source, then chamber (340) may be a polystyrene chamber. In exemplary embodiments, source (344) may be a 240-627 nm LED source connected to reflection probe (342b). Alternatively, a UV source (344) may be utilized if a wider source range is needed. In a particular embodiment, reflection probe (342b) may be the premium-grade reflection probes manufactured by Ocean Optics, Inc. See FIG. 10A. In various embodiments, the detector (346) may be a fluorometer that may require a spectral filter equal to the excitation source to filter out that light, but also detect all other wavelengths from source (344). In embodiments, detector (346) may utilize a set of photodiodes with spectral filters or a CCD. In either embodiment, the light emitted from the energy state transition, quenching, or absorption may be converted to an electrical signal by the detection system (346) and then transmitted back to the controller (332) (e.g., see FIG. 7) for identification of "fingerprint" information of the fluid sample.

Figure 11:
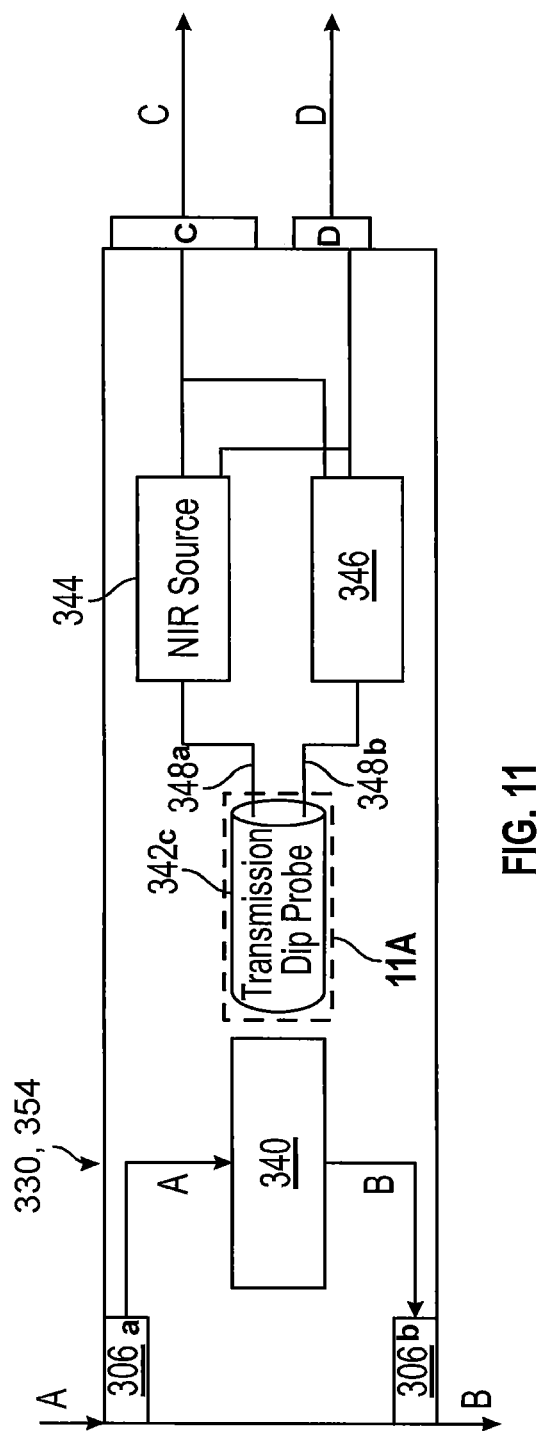
FIG. 11 is a schematic of an absorbance sub-sampling system, according to an exemplary embodiment of the present disclosure.
Figure 11A:
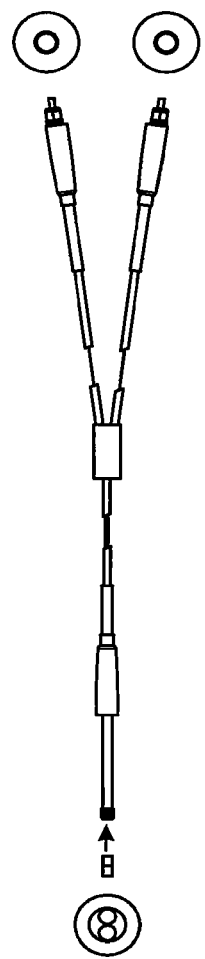
FIG. 11A is an illustration of a transmission dip probe, according to an exemplary embodiment of the present disclosure.

FIG. 11 is a schematic of an absorbance sub-sampling system (330, 354). FIG. 11A is an illustration of a type of transmission dip probe used in absorbance sub-sampling system (330, 354). Absorbance sub-sampling system (330, 354) substantially includes similar features as the sub-sampling system (330) described herein in FIG. 8, with particular modifications made to the type of probe (342c), excitation source (344), and detection system (346).

Absorbance spectroscopy, commonly referred to as spectrophotometry, is the analytical technique based on measuring the amount of light absorbed by a sample at a given wavelength. Molecular absorption spectroscopy in the ultraviolet (UV) and visible (VIS) portions of the electromagnetic spectrum relates to the measured absorption of radiation in its passage through a gas, a liquid, or a solid. Generally, the wavelength region used may be from approximately 190 to 1000 nm, and the absorbing medium may be at room temperature.

In embodiments of the present disclosure, obtaining a "fingerprint" of a sample via absorbance spectroscopy may include the same general methods as described herein for obtaining a fingerprint of a sample via fluorescence spectroscopy. In exemplary embodiments, a broadband light source may first be shined on a sample. Light coming out of the sample may then be collected and the wavelength content of the light may be analyzed. The molecular content of the sample may then be analyzed and determined by comparing the wavelength of the light that was initially sent/shined on the sample with the wavelength of the light that was collected after leaving the sample.

In exemplary embodiments, absorbance sub-sampling system (330, 354) may include a transmission dip probe (342c), a near infrared (NIR) source (344) connected to probe (342c), and a detector (346) connected to probe (342c) that measures the output (transmission) from the source (344) after passing through the sample, where the difference between the input and output is the absorption amount, i.e., the "fingerprint" of the sample. In various embodiments, chamber (340) may be a quartz flow-through cell/continuous flow chamber. In exemplary embodiments, source (344) may be a 1000-5000 nm NIR source connected to transmission dip probe (342c). Alternatively, a UV source (344) may be utilized if a wider source range is needed. In some embodiments, source (344) may include infrared and/or visible sources (usually 190 to 1000 nm). In a particular embodiment, transmission dip probe (342c) may be the TP300-Series Transmission Probes offered by Ocean Optics, Inc. See FIG. 11A. In various embodiments, the detector (346) used for detection may utilize a CCD or a set of photodiodes with spectral filters for measuring the intensity of resultant wavelengths compared to source.

Figure 12:
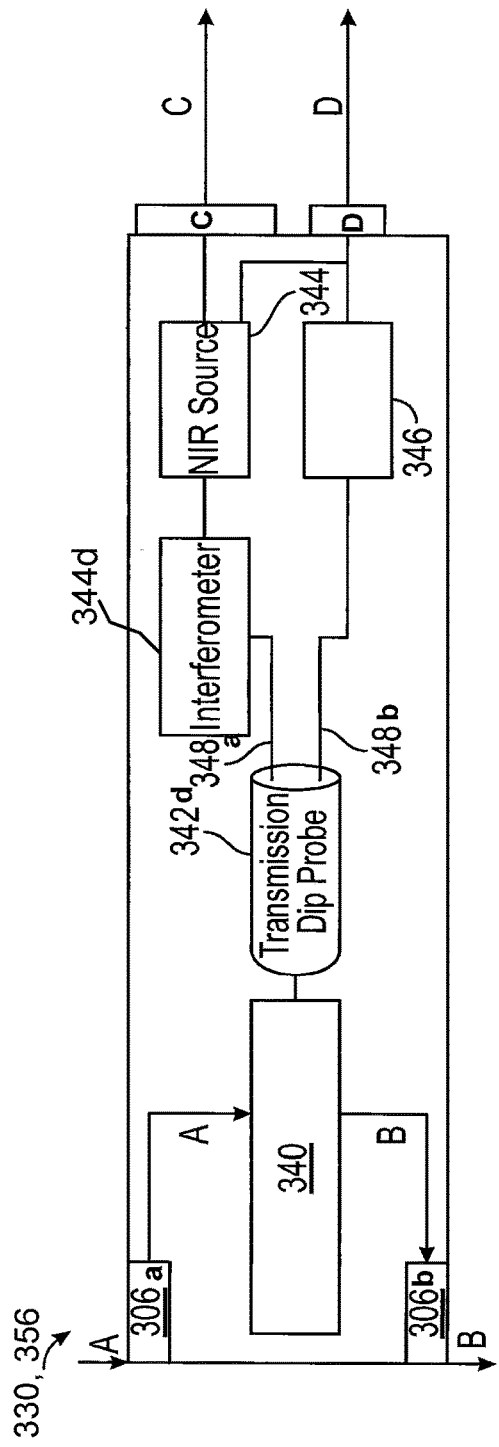
FIG. 12 is a schematic of a Fourier Transform IR absorbance sub-sampling system, according to an exemplary embodiment of the present disclosure.
Figure 12A:
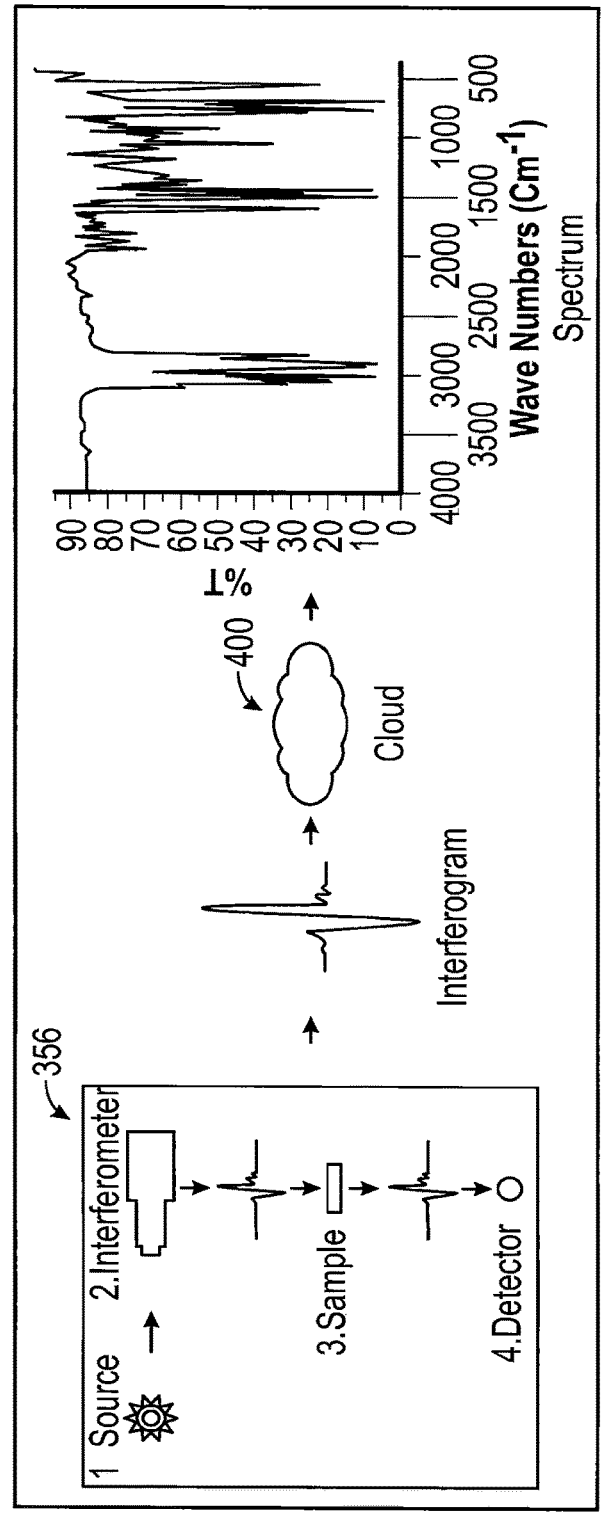
FIG. 12A is a schematic of the Fourier Transform Infrared Spectroscopy (FTIR) process in the Fourier Transform IR absorbance sub-sampling system shown in FIG. 12.

FIG. 12 is a schematic of a Fourier Transform IR absorbance sub-sampling system (330, 356). FIG. 12A is a schematic of the Fourier transform infrared spectroscopy (FTIR) process in the Fourier Transform IR absorbance sub-sampling system (330, 356). Fourier Transform IR absorbance sub-sampling system (330, 356) substantially includes similar features as the sub-sampling system (330) described herein in FIG. 8, with particular modifications made to the type of probe (342d), excitation source (344), and detection system (346).

Fourier transform infrared spectroscopy (FTIR) is a form of absorbance spectroscopy used to obtain an infrared spectrum of absorption or emission of a solid, liquid or gas. An FTIR spectrometer may simultaneously collect high spectral resolution data over a wide spectral range. In exemplary embodiments of the present disclosure, obtaining a "fingerprint" of a sample via FTIR may include the same general methods as described herein for obtaining a fingerprint of a sample via absorbance spectroscopy. For example, infrared (IR) radiation may be first passed through the sample. Some of the IR radiation may be absorbed by the sample and some of it may pass through (transmitted). The resulting spectrum represents the molecular absorption and transmission, thereby creating a molecular "fingerprint" of the sample. The "fingerprint" includes absorption peaks which correspond to the frequencies of vibrations between the bonds of the atoms making up the sample. Because each different material constitutes a unique combination of atoms, no two compounds produce the exact same IR spectrum, thereby allowing for positive identification of different kinds of material via qualitative analysis. In fact, the size of the absorption peaks in the spectrum indicates the exact amount of material present.

In exemplary embodiments, Fourier Transform IR absorbance sub-sampling system (330, 356) may include substantially the same features as absorbance sub-sampling system (330, 354), including a transmission dip probe (342d), a near infrared (NIR) source (344), and detector (346). However, Fourier Transform IR absorbance sub-sampling system (330, 356) may include an additional interferometer (344d) between source (344) and probe (348d) to measure an entire range of a wavelength of a sample at once. See FIG. 12. In various embodiments, chamber (340) may be a quartz flow-through cell/continuous flow chamber. In exemplary embodiments, source (344) may be a 1000-5000 nm NIR source connected to transmission dip probe (342d). Source (344) may be a monochromatic source. Alternatively, other sources (344) in the NIR to infrared spectrum may be used. In some embodiments, source (344) may include infrared and/or visible sources (usually 190 to 1000 nm). In a particular embodiment, transmission dip probe (342d) may be the TP300-Series Transmission Probes offered by Ocean Optics, Inc. See FIG. 11A.

In an exemplary embodiment, as shown in FIG. 12A, infrared energy/beam may be emitted from the source (344) towards the interferometer. This beam may then enter the interferometer where "spectral encoding" may take place. The resulting interferogram signal may then exit the interferometer and towards the chamber (340), where it may be transmitted through or reflected off of the surface of the fluid sample in chamber (340), depending on the type of analysis being accomplished. This is where specific frequencies of energy, which are uniquely characteristic of the sample, are absorbed. Although not shown, probe (342d) may then pick up the resulting output from the sample and pass this output to the detector (346) for final measurement. Detector (346) used may be specially designed to measure the special interferogram signal. The measured signal may then be digitized and sent to controller (332) in sampling system (304) (e.g., see FIG. 7), which may send the signal to analytical system (400) (e.g., see FIGS. 1 and 2) where the Fourier transformation may take place. Comparing the final IR spectrum to a background spectrum (measurement with no sample in the beam) may allow for identification of spectral features solely present in the sample. In exemplary embodiments, analytical system (400) may decode the signal received from controller (332) using Fourier Transform Infra-red calculations to obtain the "fingerprint" of a fluid sample.

Figure 13:
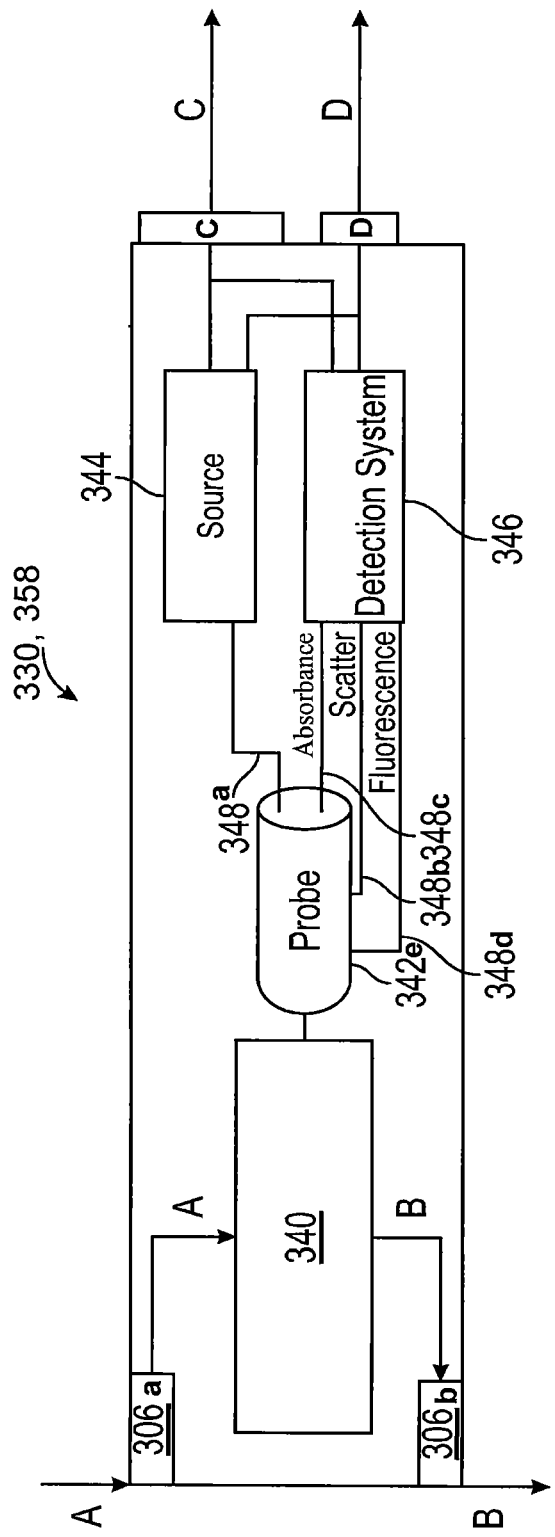
FIG. 13 is a schematic of an absorbance/fluorescence/scatter sub-sampling system, according to an exemplary embodiment of the present disclosure.

Referring to FIG. 13, a schematic of an absorbance/fluorescence/scatter sub-sampling system (330, 358) is shown. Absorbance/fluorescence/scatter sub-sampling system (330, 358) substantially includes similar features as the sub-sampling systems (330) described herein in FIG. 8, with particular modifications made to the type of probe (342e), excitation source (344), and detection system (346), as well as additional fiber optic cables (348b, 348c, 348d) between probe (342e) and detection system (346).

Particularly, absorbance/fluorescence/scatter sub-sampling system (330, 358) may combine features of both the fluorescence and absorbance sub-sampling systems (330, 352), (330, 354), described herein with reference to FIGS. 10 and 11, respectively. In exemplary embodiments, absorbance/fluorescence/scatter sub-sampling system (330, 358) may include a reflection and/or transmission dip probe (342e), multiple sources (344) connected to the probe(s) (342e), and a detection system (346) connected to the probe(s) (342e) that may measure the output (transmission) from the source(s) (344) after passing through the sample, where the difference between the input and output is the absorption amount, i.e., the "fingerprint" of the sample. In various embodiments, chamber (340) may be a quartz flow-through cell/continuous flow chamber. In exemplary embodiments, sources (344) may include multiple sources independently connected to reflection and/or transmission dip probes (342e) via fiber optic cables (348a). For example, LED source and/or UV source may be connected to a reflection probe (342e), while a 1000-5000 nm NIR source may be connected to a transmission dip probe (342e). In a particular embodiment, transmission dip probe (342e) may be the TP300-Series Transmission Probes offered by Ocean Optics, Inc. See FIG. 11A. In an exemplary embodiment, reflection probe (342e) may be the premium-grade reflection probes manufactured by Ocean Optics, Inc. See FIG. 10A. In various embodiments, the detection system (346) may utilize a CCD or a set of photodiodes with spectral filters for measuring the intensity of resultant wavelengths compared to the source (344). In example embodiments, the use of multiple sources (344) may require additional fiber optic cables (348b, 348c, 348d) connected to probe (342e) with multiple "eyes" for each cable (348b, 348c, 348d), i.e., a different set of photo diodes in detection system (346) for detection of fingerprint data from the sample for each type of spectroscopy system used. Using additional fiber optic cables (348b, 348c, 348d) may allow for the measurement of different types of fingerprint data by choosing to apply or not apply a spectral filter for an excitation source (344) wavelength to cable (348b, 348c, 348d).

Although particular embodiments described herein refer to analysis of oil, fluid analysis system (100) as described herein, including cooling system (302), sampling system (304), and/or analytical system (400) described herein may be used to analyze properties of other types of fluids, including water (e.g., see FIGS. 1 and 2). In an exemplary embodiment, fluid analysis system (100) described herein may be a water analysis system (100). In embodiments of this water analysis system (100), water may be routed from a water source (200), e.g., a reservoir, into cooling system (302) and/or directly into sampling system (304) to obtain real-time data regarding the fluid. For example, water may be analyzed in embodiments of the present disclosure to determine the presence of microorganisms, nitrate, and arsenic.

In various embodiments, cooling system (302), sampling system (304), and/or analytical system (400) of water analysis system (100) may include substantially the same features as oil analysis systems (100) described herein (e.g., see FIGS. 1 and 2). However, in some embodiments, cooling system (302) of water analysis system (100) may not include a filter (320). As in oil analysis system (100), cooling system (302) may not be utilized in water analysis system (100) if water is at a sufficiently low temperature for analyzing via sampling system (304). In various embodiments, sampling system (304) of water analysis system (100) may or may not include a viscometer (328) (e.g., see FIG. 7).

Although fluid analysis system (100), including oil analysis system (100) and water analysis system (100), are shown in FIGS. 1 to 13 and described herein as having specific configurations/features/applications, these systems are not limited to these particular configurations/features/applications and other configurations/features/applications may be utilized as suitable to perform analysis of various types of fluids.

Figure 14:
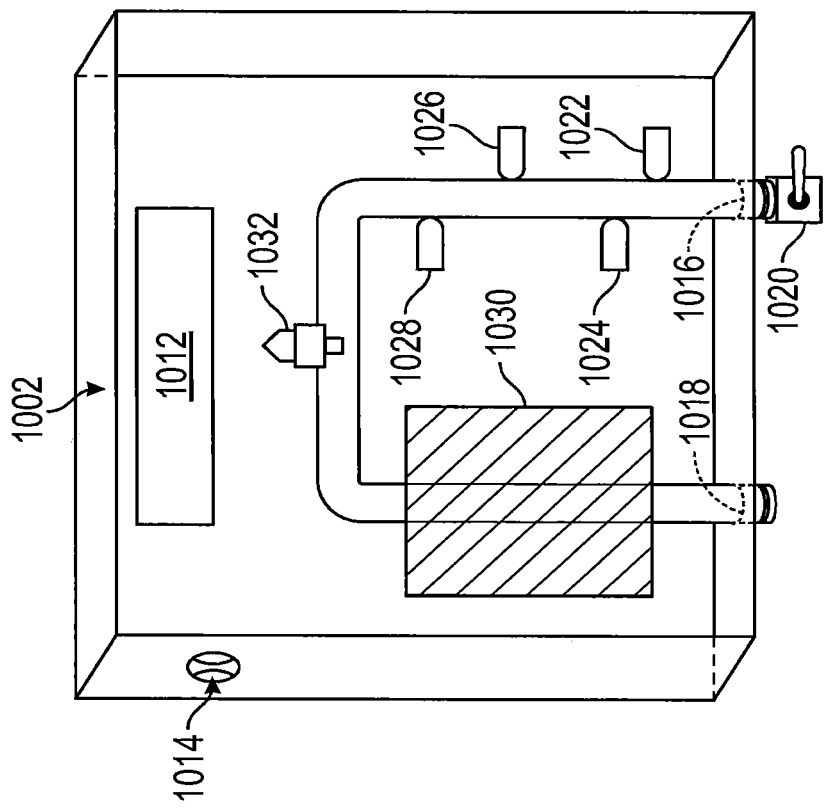
FIG. 14 is a schematic of a fluid analysis system with a nano chip plug, according to an exemplary embodiment of the present disclosure.
Figure 14:
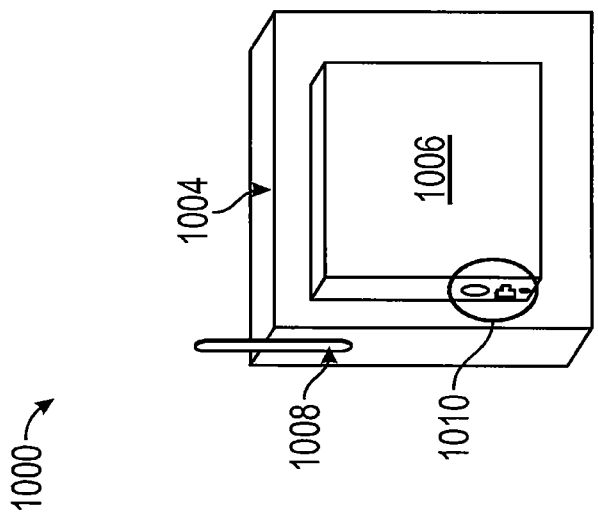

Referring to FIG. 14, a schematic of an alternative embodiment of fluid analysis system (1000) with a nano chip plug (1032) is shown. Fluid analysis system (1000) may include an enclosure (1002) having a female pipe thread inlet (1016) and outlet (1018). In an exemplary embodiment, enclosure (1002) may be an 18 in×18 in×6 in metal enclosure, and inlet (1016) and outlet (1018) may be ¼ inch inlets and outlets. In various embodiments, the inlet of enclosure (1002) may include a shut-off valve (1020) built into the design for safety (in case a line is leaking in the circuit) and/or for maintenance that may need to be performed on the enclosure (1002) without having to shut the system (1000) down. Additionally, enclosure (1002) may include a reset switch (1014) on one side for manual reset of the engine/equipment after an oil change has been performed to establish a new baseline for oil analysis.

Enclosure (1002) may also include a controller (1012) with the ability to control up to 36 fluid analysis sensors. Fluid analysis sensors may be mounted within enclosure (1002). For example, enclosure (1002) may include multiple types of oil analysis sensors, including but not limited to sensors with the following properties: oil property monitoring capabilities, and/or identification of specific wear metals (1022), moisture levels (1024), particulate counts (1026), viscosity (1028), TAN, TBN, Nitration, Sulfation, Foreign Oils, Solvents, Glycol, Soot, Dissolved Gases, and/or Oil Additive Depletion (Zn, Mo, Ph, Ca, Mg, Ba, Na). See, e.g., FIG. 14. Sensors may be programmed to communicate data every two seconds to few minutes to the controller (1012) with a lifespan of five years or longer. In some embodiments, sensors may be provided that may be easily changeable if replacement is required. To replace a sensor, shut off the built in shut off valve (1020), open the front cover panel, unscrew the sensor from the controller (1012), and unscrew the sensor from the female pipe thread. Once unhooked, replace, and reattach new sensor in the same manner. Controller (1012) may be configured to automatically recognize the new sensor and start collecting data.

In some embodiments, enclosure (1002) may include an electric pump (2004) (e.g., see FIG. 16) that may draw oil out of the attached equipment/engine, and push the oil through the enclosure (1002) and back to the equipment/engine. Pump may be a 120 v, 240 v, or 480 v electrical pump. Enclosure (1002) may further include a built in pressure reducing valve on the inlet pressure line. In an exemplary embodiment, the pressure reducing valve may reduce oil pressure from 5000 psi down to 50 psi before it goes through the enclosure (1002) and back to the equipment/engine.

In various embodiments, enclosure (1002) may include a 1-micron oil filter (1030). Oil may flow through the system (1000) in a particular sequence to validate and ensure extended life of the equipment's oil. In an embodiment, the system (1000) may be configured in the following order: Wear metal sensor (1022), Water Sensor (1024), Particle Count Sensor (1026), Viscosity Sensor (1028), Oil Parameters Sensor, 1-Micron Oil Filter, Particle Count Sensor, Oil Parameter Sensor (e.g., see FIG. 16). This sequence may be important in determining the oil purity of the equipment since the 1-micron filter may change the particle count and moisture content in the oil. System (1000) may extrapolate the wear metals, water, particle count, viscosity, and parameters before the oil crosses the 1-Micron filter. System's (1000) ability to calculate the difference between the readings before and after the 1-Micron filter (as described below with reference to FIG. 16) may allow for accurate oil quality measurement and oil life predictive calculations. Since these readings may be on both sides of the 1-Micron filter, a true reading of the oil and equipment condition may be realized in the reading (e.g., see FIG. 16 and related description). Taking readings in this order, on both sides of the 1-micron filter, may thus further improve predictability of the lifecycle of the oil and equipment condition.

In exemplary embodiments, system (1000) may further include a node enclosure (1004) connected to enclosure (1002). See FIG. 14. Node enclosure (1004) may be a 12 in×12 in×6 in weatherproof enclosure with an antenna (1008) for satellite, cell phone, or Wi-Fi connectivity. Node enclosure (1004) may track up to six different data inputs into one account. Each data point may relate to a separate enclosure (1002) that may be hard wired back to the node enclosure (1004). In addition to the six hard wired enclosures, system (1000) may be piggy backed together with other systems (1000) for up to 36 different systems (1000) and route back into one connection at the node enclosure (1004). This particular configuration may allow for system (1000) to only have one communication node for multiple enclosures (1002)/systems (1000), provide great cost benefits to the consumer, and allow for easier and cleaner installation of the system (1000). Node enclosure (1004) may further include a connection for satellite/Wi-Fi/cell tower antenna (1008) and a power port and/or Ethernet/HDMI port (1010).

Node enclosure (1004) may be outfitted with a rugged node (1006) for custom programming and algorithms to compute and process sensor inputs and to relay crucial notification abilities via text or email. The programming and algorithms may include oil analysis readings for the following: specific wear metals, moisture levels, particulate counts, viscosity, TAN, TBN, Nitration, Sulfation, Foreign Oils, Solvents, Glycol, Soot, Dissolved Gases, and/or Oil Additive Depletion (Zn, Mo, Ph, Ca, Mg, Ba, Na). The custom programming may also send instant notifications to the user the moment critical levels are reached as established by user-determined preferences or as determined by the NIST (National Institute of Standards and Technology) oil analysis standards if there are no user-determined preferences are not programmed into the node (1006). The programming and algorithms may have a predictive ability built into the design of the node (1006) that may notify users of upcoming preventive maintenance.

In various embodiments, networking capabilities of the system (1000) may be virtually limitless due to the ability of system (1000) to piggyback enclosures (1002) together. Networking features include: (i) daisy chaining up to 36 enclosures (1002) going to one node enclosure (1004); or (ii) wiring up to 36 enclosures (1002) into the node enclosure (1004) directly. Once these multiple enclosures (1002) are transmitting data into the node enclosures (1004), system (1000) may combine an unlimited number of data points into on account that may be accessible by the user on a 24×7 basis via any internet connected device. This may afford the user full control over the monitoring and maintenance of its equipment/engine.

In an exemplary embodiment of the present disclosure, oil may be re-routed from the equipment through the systems described herein, and back to the equipment. Once oil is flowing through the system, wear metals, moisture levels, particulate counts, viscosity, TAN, TBN, Nitration, Sulfation, Foreign Oils, Solvents, Glycol, Soot, Dissolved Gases, and/or Oil Additive Depletion (Zn, Mo, Ph, Ca, Mg, Ba, Na), and/or oil temperature reporting may be tested and logged up to every 2 seconds. In some embodiments, an additional sensor may be added for emissions monitoring. Each different measurement may be taken via a specific sensor for each analysis data point. The data may be collected into controller (1012) built into the enclosure (1002) described herein. Controller (1012) may transmit the data to the node (1006). In exemplary embodiments, node (1006) may be a small Linux based computer. Node (1006) may be programmed with custom algorithms to compute and process the sensor inputs from the controller (1012), and to relay crucial notifications. Node (1006) may then transmit the data through the best available method: Ethernet cable, Wi-Fi, cell phone signal, or satellite signal.

Once this data is transmitted, it may be stored in the cloud and the data may be readily available for the user to access from their computer, tablet, or phone. If internet signal drops, node (1006) may be fitted with a 60 gigabyte hard drive that may store the information until the internet signal is restored. Once internet is restored, node (1006) may automatically dump all of the data to the cloud based storage. If there is critical information gathered from the system, the user may be notified via text or email. User may log into their account with custom designed dashboards so they can see all equipment and data points being monitored. Custom dashboards and alerts may be determined by the user to meet its individual needs. Alerts may be sent to the user via email or text message automatically from the system algorithms that may be programmed for specific data points. The online dashboard may be web-based and may be accessed from any device that has an internet connection. The dashboard may automatically collapse and stack the data to for e.g. a tablet and/or cell phone view if the user is not logging in from a computer/web browser.

Once this system (1000) is installed and parameters have been programmed into the node (1006), the user may be completely independent from the supplier in the management and maintenance of its equipment. For a customer to be completely independent from any oil lab, oil tech, mailing company, and/or technician taking oil samples gives the customer assurance of lack of human errors or time delays of this critical data during the systems process. Further, if the user's needs evolve, additional data points may be programmed into the node (1006) if required. If a customer uses a unique type of oil or wants custom notifications when the system (1000) reads any key components from the built in sensors, system (1000) may be custom programmed for that customer's needs. This type of custom programming may be important for larger customers having engine manufacturers that require certain key elements monitored.

In some embodiments, the system (1000) described herein may be used to perform real time oil analysis sampling from multiple pieces of equipment. Sampling from multiple pieces of equipment may be accomplished through customized multi-flow control valves that may allow oil to be brought in from multiple pieces of equipment using the same type of oil. In embodiments, the pieces of equipment may be located in the same vicinity as each other and system (1000). In other embodiments, the pieces of equipment may be located further away/remotely from each other and system (1000).

Multi-flow control valves may be controlled via custom designed dashboards as described herein. Multi-flow control valves may be configured as manifold-control valve connections. Flow control valves may be inlet multi-flow control valves and/or outlet multi-flow control valves. System (1000) may include an inlet multi-flow control valve programmed to allow oil to flow into an enclosure (1002) from only one engine at a time via an inlet valve described herein (e.g., see FIGS. 4 and 6). System (1000) may further include an outlet multi-flow control valve programmed to allow for the oil to be returned to the same engine from which it was pulled via an outlet valve described herein and a return line going back to the same equipment (e.g., see FIGS. 4 and 6). In an exemplary embodiment, once an analysis is made over a period of 2 to 5 minutes, the inlet valve may switch off, at which time the system may be programmed to notify another valve to open for a next piece of equipment that may have been programmed in a sampling sequence. In some embodiments, a delay of 60 to 180 seconds may occur between the opening of a new valve and for the system (1000) to start taking readings to clean out the lines feeding the system (1000). In other embodiments, this sequence of changing between different pieces of equipment may be programmed from every few minutes, to once an hour, per piece of equipment depending on a customer's needs.

In exemplary embodiments, once system (1000) is taking readings from each different motor/equipment in the area, it may be configured to then run comparative algorithms in a separate custom designed dashboard described herein, and thereby perform comparative analysis of oils from different equipment to determine which engines may be running most efficiently and which engines may be in need of extra attention, modifications, and/or service. Detailed reporting may allow for customers to pinpoint any problems with efficiency in different pieces of equipment and solve any problems that they may not have known existed. Further, this reporting may also allow the customers to determine themselves which engines are running most efficiently and which engines may need to be replaced.

Figure 15:
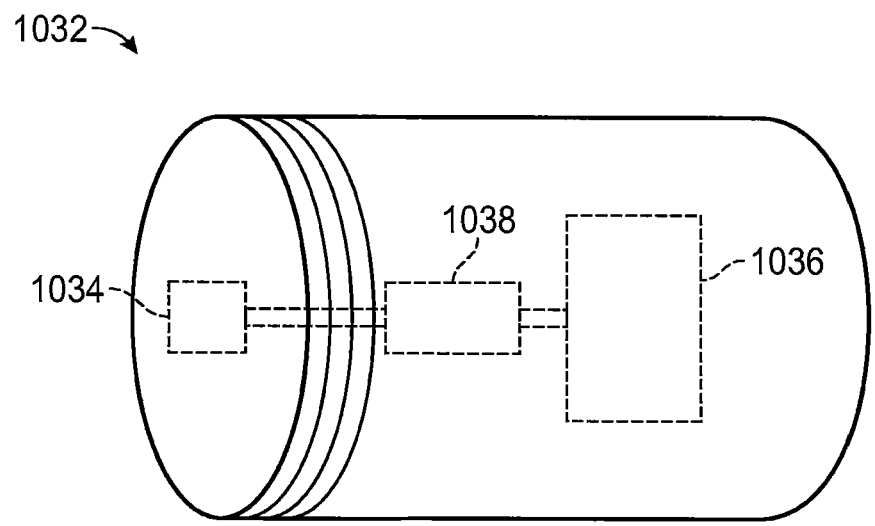
FIG. 15 is an illustration of interior components of a nano chip plug for use in a fluid analysis system, according to an exemplary embodiment of the present disclosure.

In particular embodiments, system (1000) may be retrofitted with a nano chip plug (1032) technology (e.g., see FIGS. 14 and 16) to perform real time oil analysis of a fluid after the fluid has passed through several sensors (1022, 1024, 1026, 1028) as described herein. See FIG. 14. FIG. 15 is an illustration of interior components of the nano chip plug (1032). Nano chip plug (1032) may utilize a spectral scanner/spectrometer (1034) to instantaneously and continuously scan and inform a user of the molecular makeup and condition of any industrial oil. As described herein, different types of fluids/materials have their own "fingerprint" and nano chip plug (1032) may read and analyze the differences between these materials and obtain this "fingerprint" information of the fluids via spectroscopy. In exemplary embodiments, nano chip plug (1032) may have a size less than approximately 1 inch×1 inch. In other embodiments, the nano chip plug (1032) may have other sizes and configurations to perform real time oil analysis. Embodiments of the present disclosure provide for several different options that may cover a variety of industries and applications, including but not limited to oil and gas, maritime, aerospace, government, agriculture, water, waste water, lube oils, hydraulic oils, gear oils, coolants, etc. Embodiments of the systems described herein may be able to work with any type of industrial fluid.

In exemplary embodiments, nano chip oil plug (1032) may be used for real time oil analysis by integrating a nano chip and spectrometer (1034) into an oil plug. See, e.g., FIG. 15. The oil plug may be any plug that may access the fluid being analyzed. In an exemplary embodiment, an existing oil plug in an engine/equipment may be removed, and a nano chip oil plug (1032) may be installed onto the engine/equipment in place of the existing oil plug.

Embodiments of the present disclosure may further utilize a database as described herein in conjunction with the systems described herein. In an exemplary embodiment, a "fingerprint" of a sample of a particular type of oil [for e.g., Shell Rotella® 15W-40] in a particular engine [for e.g., Caterpillar Cat® 3516B diesel generator] may be analyzed and collected via the system (1000) with the nano chip plug (1032). This "fingerprint" information may then be transmitted to a node (1006) as described herein, which may then transmit this information to a database as described herein via any of the systems described herein. Database (e.g., system 1000 of FIG. 14) may then compare this fingerprint information to existing information stored in the database for that particular type of oil and its conditions, including but not limited to the presence of any wear metals in the oil being analyzed. In a particular embodiment, node (1006) (e.g., see FIG. 14) may connect to the cloud and run a comparative analysis algorithm between this fingerprint information and existing information on the database for the same type of oil to determine a precise makeup of this particular oil sample. Doing so may allow for the detection of the presence of several conditions in this oil sample, including but not limited to the presence of wear metals, as well as the diagnosis of any particular problems with the engine. In exemplary embodiments, this process involving comparison and analysis of the current and existing real-time data may only take about 2 to 30 seconds. System (1000)/database may then relay the conclusions from this comparative analysis to customers requesting the information. In embodiments, this information may be sent to customers via email, text, website software, and/or any other available methods of communicating such information.

By comparing new scans to the existing database of sample scans, system (1000) may instantaneously provide the condition of the fluid sample. In some embodiments, system (1000) may be continuously grown by scanning and adding additional sample types as they become available, thus increasing the accuracy of the overall system's detecting abilities. Database may be accessed via the internet, cell phone signal, satellite connection, and/or any other available connection to external sources. In various embodiments, database may be grown via "training" in a neural network as described herein.

Figure 16:
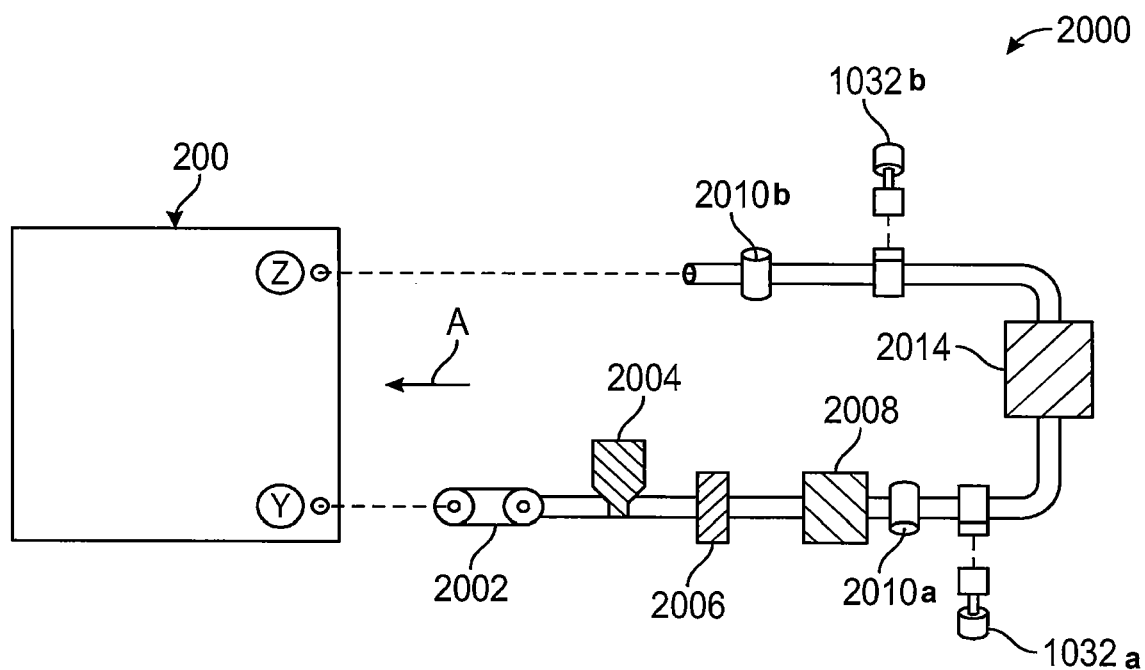
FIG. 16 is a schematic of a fluid analysis system with a nano chip plug, according to an exemplary embodiment of the present disclosure.

FIG. 16 is a schematic of an alternative embodiment of fluid analysis system (2000) with the nano chip plug (1032) described herein. As shown, fluid analysis system (2000) with the nano chip plug (1032) described herein may be constructed to install at an engine oil pressure galley and bypass the engine back to the oil filler neck. In the bypass loop, oil may be flowed/routed from equipment fluid access point, Y, through a programmable flow control valve (2002). Flow control valve (2002) may be programmed to open and close to allow oil to flow through system (2000). Oil may be stationary in the system (2000) once the valve (2002) is closed during a scan. This option may be added to allow for a more detailed oil sample to scan the oil while it is stable and not flowing at, for e.g., 50 psi. Once the scan is complete, the valve (2002) may open and allow oil to flow through the system (2000) until the next sampling time. In exemplary embodiments, this next sampling time may occur as soon as every 30 seconds. However, this system (2000) may be configured to take samples in any other time as needed.

Oil may be routed through a pump (2004) to provide pressure when there is no oil/fluid pressure available. See FIG. 16. In various embodiments, oil may then be routed through a pressure reducing valve (2006), oil cooler (2008), and push button oil sample valve (2010*a*) installed for sampling of the oil before it reaches nano chip plug (1032*a*). Oil cooler (2008) may be used inline if the oil being routed through the system (2000) is too hot. From nano chip plug (1032*a*), oil may be routed to a 1 micron bypass oil filter (2014) to allow for more detailed analysis and further prolong engine oil life via extra filtration of the oil sample. In exemplary embodiments, another nano chip plug (1032*b*) may be added after the 1 micron bypass oil filter (2014). The 1 micron oil filter (2014) may be inline of a bypass loop and may take a scan before and after fluid/oil passes through the filter (2014) in order to compare and determine how well the filtration is performing and how exactly the filter (2014) is impacting the fluid/oil sample. This particular configuration is unique because once this additional nano chip plug (1032*b*) is added, the before and after readings of the samples may be compared and analyzed, which data may then be used to prolong the life of the oil and provide a measurable impact that the filter (2014) may be having on the oil. In contrast, it is virtually impossible to show the measurable impact of an oil filter (2014) in real time in existing systems. On the way back to the engine's oil filler neck into equipment's fluid return point, Z, oil may be passed through another push button oil sample valve (2010*b*).

Fluid analysis system (2000) may be used to gather samples and/or add relevant data from the samples to a database. Fluid analysis system (2000) may be connected to and transfer data from the samples to a node (1004) (e.g., see FIG. 14) as described herein, which may then transmit the data to a database as described herein. Database may be located in the cloud or in any known external device. In some embodiments, the node itself may house the database.

Figure 17:
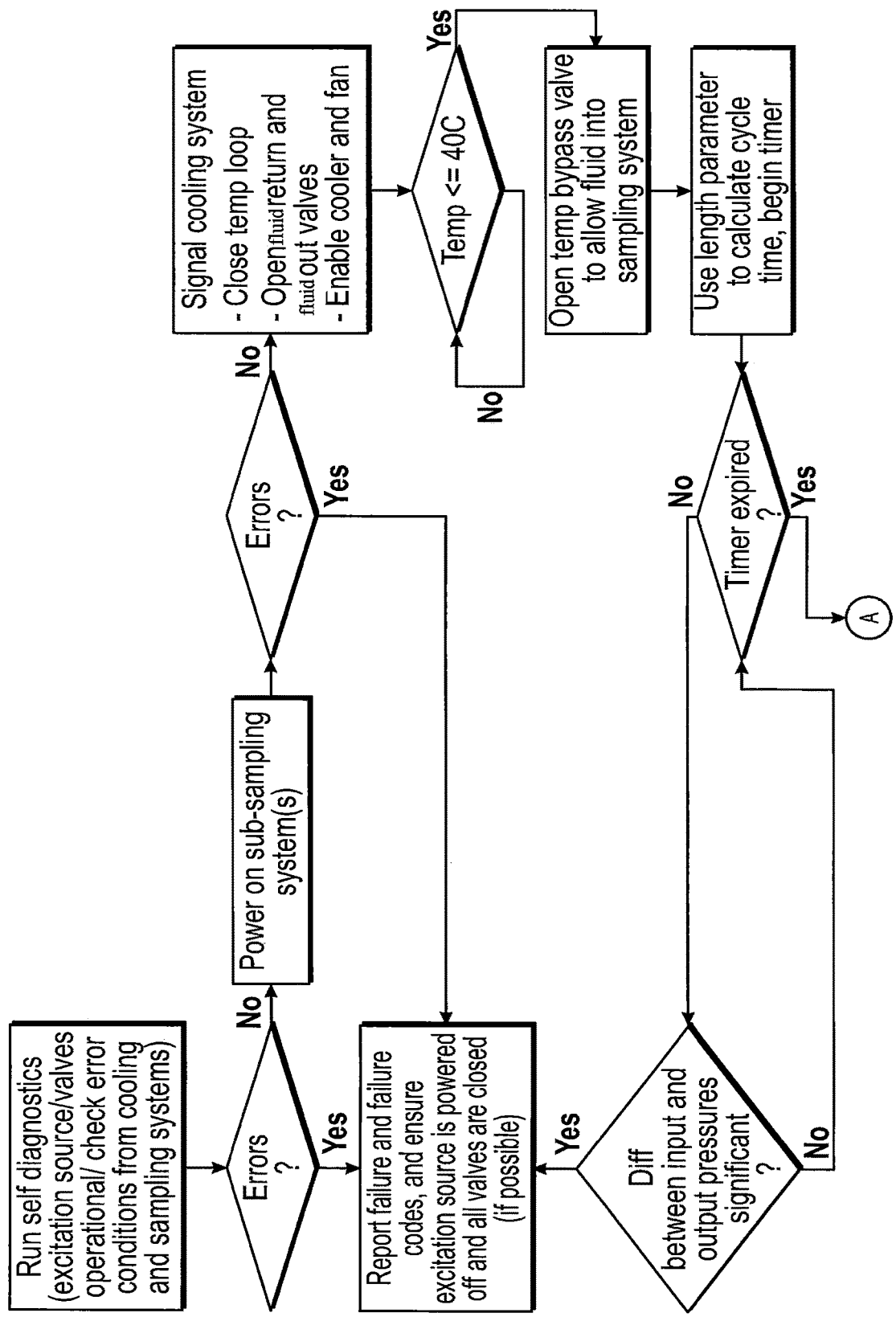
FIG. 17 is a flowchart of a fluid analysis system, according to an exemplary embodiment of the present disclosure.
Figure 17:
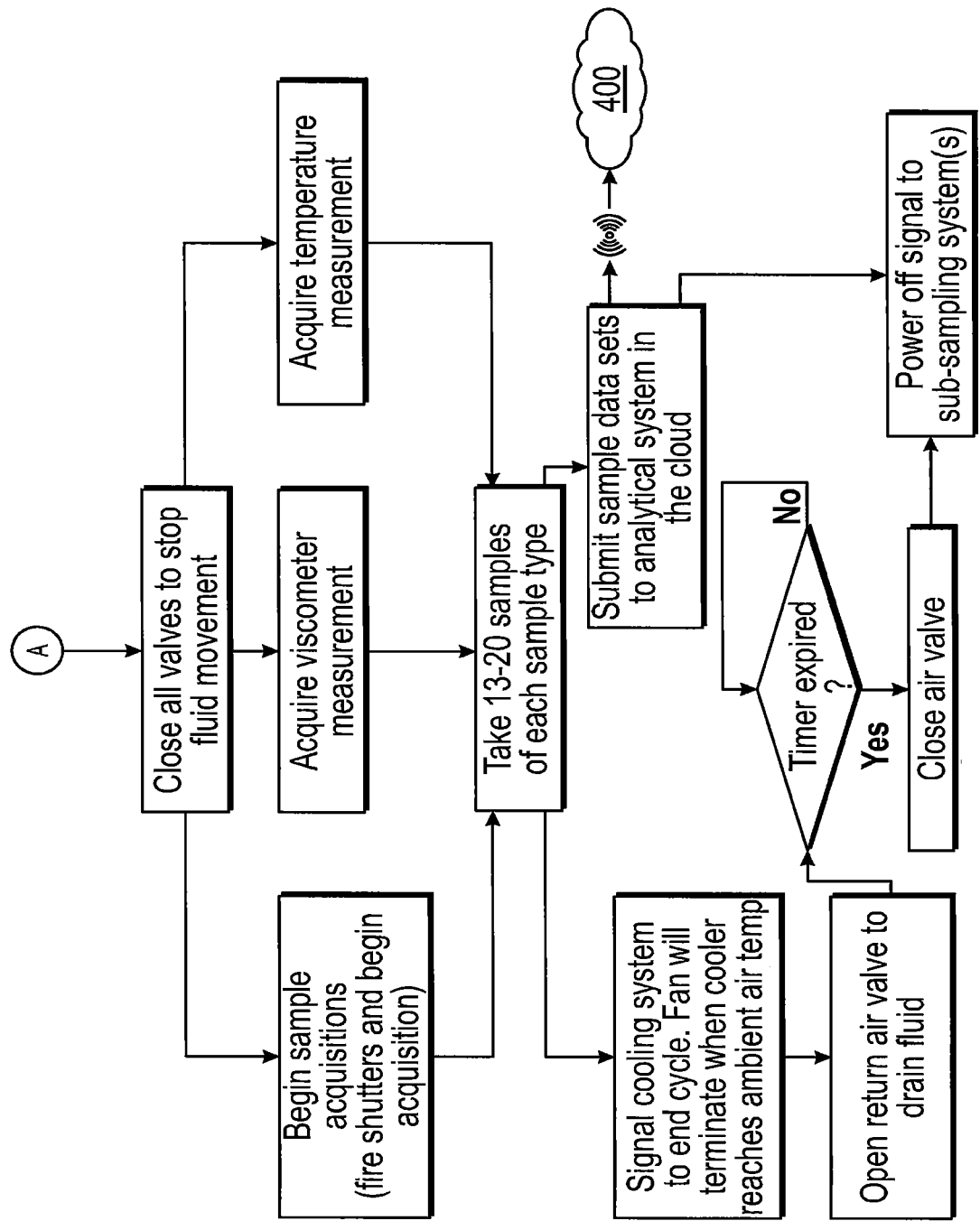

FIG. 17 is a flowchart of a fluid analysis system (100) as described herein using cooling system (302) and sampling system (304), including related software in controller (332) (e.g., see FIG. 7) of sampling system (304) and/or cooling system (302), as described herein (e.g., see FIGS. 1 to 6). Fluid analysis system (100), cooling system (302), and sampling system (304) described in FIG. 17 may be implemented using the apparatuses, systems and methods described herein, including various embodiments thereof. As shown in FIG. 17, fluid analysis system (100) may include the following steps.

In an exemplary embodiment, software of controller (332) (e.g., see FIG. 7) of sampling system (304) may first run a self-diagnostics check to determine whether excitation source (344) and/or valves (312 and 314*a* to 314*d*) are operational and for any error conditions from cooling system (302) and sampling system (304). If the initial self-diagnostics check shows error conditions, controller (332) may report these errors/failures and any related failure codes to the analytical system (400), and ensure the excitation source (344) is powered off and that all valves (312 and 314*a* to 314*d*) are closed (if possible). If the initial self-diagnostics check does not show any error conditions, then sub-sampling system (330) may be powered on. Again, if error conditions arise, controller (332) may report these errors/failures and any related failure codes to analytical system (400), and ensure the excitation source (344) is powered off and that all valves (312 and 314*a* to 314*d*) are closed (if possible). If no error conditions are produced upon powering on of the sub-sampling system (330), controller (332) may send a signal to cooling system (302) to close the temperature loop described herein relating to action of pressure reducer valve (308. 308*a*, and 308*b*) (e.g., see FIGS. 3 to 7), cooler (324), temperature sensor (310), and 2-way solenoid valve (312), open fluid return and fluid out valves (314*a* to 314*d*), and enable cooler (324) and fan (370) to cool fluid.

If the temperature >40° C., oil may be re-routed back to cooler (324) as described herein for further cooling. If the temperature <=40° C., bypass valve (312) may be opened to allow fluid through to sampling system (304). Once in sampling system (304), controller (332) may use a length parameter to calculate overall cycle time and begin a timer. Particularly, if there are multiple fluid sources (200), and one source (200) is significantly further away from another source (200), sampling system (304) may have to cycle the fluid for a longer time to ensure the sub-sampling system (330) is not contaminated. If the timer has not expired, controller (332) may utilize sensor/transducer (308B) located at output/return line of sampling system (304) (e.g., see FIG. 7) to perform a pressure comparison between the input and output pressures to determine if a significant enough drop exists to identify the presence of a leak. If so, controller (332) may report this failure and any related failure codes to analytical system (400), and ensure the excitation source (344) is powered off and that all valves (312 and 314*a* to 314*d*) are closed (if possible).

If the difference between the input and output pressures is not significant, controller (322), and the timer has expired, controller (332) may close all valves (312 and 314*a* to 314*d*) to stop movement of the fluid and begin sampling of fluid using sampling system (304) as described herein. In various embodiments, sampling system (304) may then begin fluid sample acquisition as described herein, use viscometer (328) to obtain viscosity measurement of the fluid, and/or use temperature sensors (310) to measure temperature of the fluid as described herein (e.g., see FIG. 7). In exemplary embodiments, sampling system (304) may then take 13 to 20 samples of each sample type and send these sample data sets to controller (332), which controller (332) may then submit the sample data sets to analytical system (400) as described herein.

In various embodiments, controller (332) may send a signal to cooling system (302) to end its cycle. For example, fan (370) may terminate when cooler (324) reaches an ambient air temperature as described herein. Once the fluid is adequately sampled by sampling system (304), fluid may be routed back from sampling system (304) to cooling system (302). To facilitate this return, controller (332) may open return air valve (322) (e.g., see FIGS. 3 to 6) in cooling system (302) as needed to allow air to purge the line and speed up the return of fluid if there is no pressure to push/gravity drain the fluid back into cooling system (302) from sampling system (304). Controller (332) may then determine whether the timer described herein has expired. If so, controller (332) may close air valve (322) and power off sub-sampling system (330) and/or sampling system (304).

Figure 18:
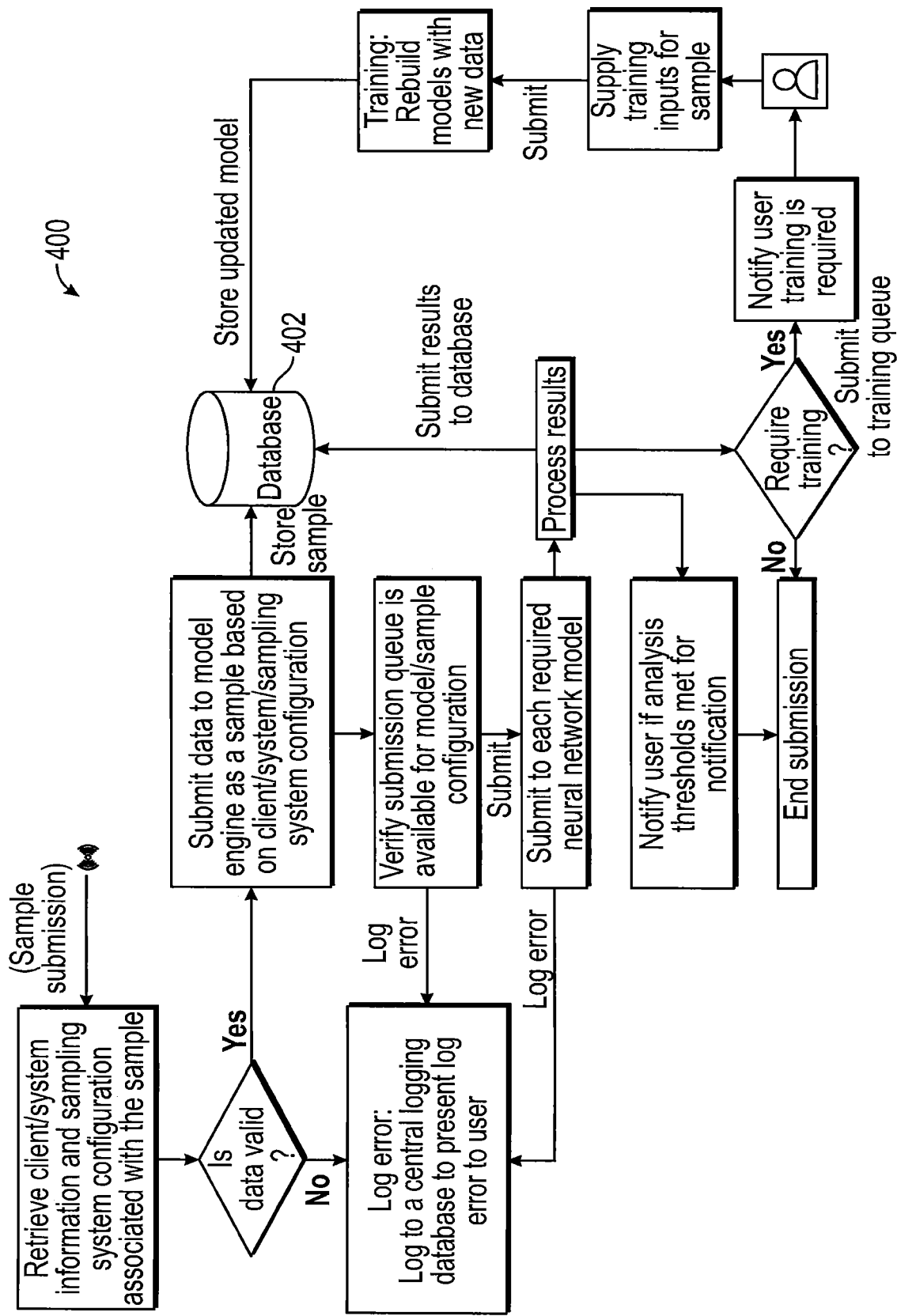
FIG. 18 is a flowchart of an analytical system, according to an exemplary embodiment of the present disclosure.

FIG. 18 is a flowchart of analytical system (400) as described herein, including command and control system (406) and database (402) described herein. Analytical system (400), command and control system (406), and/or database (402) described in FIG. 18 may be implemented using the apparatuses, systems and methods described herein, including various embodiments thereof.

As described herein, command and control system (406) may be a hosted software system that may receive the submitted sample data sets of the fluid and process it through a set of neural network models for predictive analysis. The neural network models may be configured to target any type of fluid to be analyzed. The resulting output of the sample analysis may be dependent on the fluid submitted, the networks processed and the statistical percentage accuracy for the given network model.

The output from a spectral sample is known as a spectral wave. This may be visualized as a set of coordinate points, x (usually for wavelength or in Raman the shift), and Y (usually an intensity value seen at that wavelength point). These graphs of data (points) may then be uploaded to the analytical system (400) where it may be stored, assessed and presented to a neural network model for concrete identification and system prediction. In order for spectral samples to have any context, known samples must be obtained prior to receiving fluid samples so that a baseline may be established for a specific neural network. A neural network may be composed of three layers: an input layer, hidden layer, and output layer, with each layer including one or more nodes where information flows between the nodes.

If the type of sample cannot be identified, neural networks may require "training", i.e. inputting of known parameters associated with types of samples/sub-sampling systems (330) to assist in identification of the samples and strengthen the resulting neural network model. A neural network model represents the knowledge of the neural network. As described herein, a neural network model may be created from known data sets. Therefore, when a sample is submitted, the parameters for which the sample was collected may be required to identify the particular neural network to use for identification. For example, a neural network for the fluid analysis systems (100, 1000, 2000) (e.g., see FIGS. 1, 2, 14, and 16, respectively) described herein may be defined by the following set of parameters, including but not limited to the type of sub-sampling system (330) used, wavelength of electromagnetic radiation (or if it's monochromatic), viscosity, temperature, and pressure. These parameters may define the network and its' subsequent model. Known data sets, i.e., a spectral sample of fluid (e.g., clean oil) with x ppm of y elements combined with the above determined parameters may allow for "training" of a network and creation of a model. The more known (good) data that can be trained into a neural network, the higher the accuracy and success rate of identifying unknown samples. In exemplary embodiments, building neural network models may require the use of immense computational resources. To that end, building of these models may occur in the analytical system (400) in the cloud with models potentially pushed to the sampling system (304) if onboard analysis is required.

In exemplary embodiments, a user may access and/or modify the analytical system (400) via for e.g. a web application (HTTP/HTTPS) in a computing device through any type of encrypted connection described herein. In exemplary embodiments, user may log in to the database (402), and based on his/her role and security permissions, be shown a dashboard of available sampling systems (304), messages (either predictive analysis messages based on samples), error messages, and/or training request messages. In various embodiments, the user may select a specific sub-sampling system (330), interact with the sampling system (304) and ask the sampling system (304) to perform analysis and obtain a fluid sample, configure the system (304) (i.e., setup the automated sampling timeframe), analyze the real time parameters coming from the system (304) (for e.g. temperature, last time sample taken, pressure, fluid temperature, etc.). In some embodiments, the user may also add new sub-sampling systems (330) to a client and/or de-authorize or shutdown existing sampling systems (330). User may also, if available, issue a software update to sampling system (304) and/or cooling system (302), view analytical neural networks and related network statistics, and also view the number of known good samples, percentage of successful identification, accuracy threshold, and/or force a retrain or model diagnostic.

Referring back to FIG. 18, analytical system (400) may include the following steps. Command and control system (406) of analytical system (400) may first receive submitted sample data sets of the fluid being analyzed from controller (332). See FIG. 17. Upon receipt of these sample data sets, command and control system (406) may first retrieve client/system information and sampling system (304) configuration associated with the sample. If the client/system information and sampling system (304) configuration cannot be retrieved from the submitted sample data sets, system (400) may show a "log error" and command and control system (406) may interact with database (402) to present this log error to a user via web application as described herein, so that the user may make appropriate modifications as necessary. If the data is valid, command and control system (406) may submit the data sets to a model engine as a sample based on the client/system/sampling system (304) configuration. In exemplary embodiments, command and control system (406) may also store this sample data set in database (402) described herein.

Command and control system (406) may then verify that a submission queue is available for a specific model/system configuration. For example, if the sample is a type of oil with a viscosity of X, and Raman sub-sampling system (330, 350) with a wavelength of 785 nm is used to perform analysis of the oil, command and control system (406) may search the database (402) for and utilize a model matching those exact parameters to determine the identity of the sample of oil.

If a submission queue is not available, system (400) may show a "log error" and command and control system (406) may interact with database (402) to present this log error to a user via web application as described herein, so that user may make appropriate modifications as necessary. If a submission queue is available, command and control system (406) may then submit each data set to the corresponding neural network model as described herein. Neural network model may then process results based on each data set as described herein, which results may then be sent to database (402) by command and control system (406). If any issues arise with submitting each data set to the neural network model, system (400) may show a "log error" to user as described herein.

Once fluid analysis results are processed by a neural network model, command and control system (406) may notify the user if these results meet certain defined analysis thresholds for the samples/type of sampling system (330). If so, command and control system (406) may end submission of the data sets to the neural network model.

Command and control system (406) may then determine whether the system requires "training" as described herein.

If not, command and control system (406) may end submission of the data sets to the neural network model. However, if the system does require training, command and control system (406) may notify the user that appropriate training is required. In exemplary embodiments, user may then (via a web application) supply certain training inputs to command and control system (406) for each sample for which training is requested. Command and control system (406) may use these training inputs to update/rebuild the neural network models or create new neural network models with the new data obtained from the fluid sample data sets. Command and control system (406) may then store the updated/new models in database (402), and/or deploy the updated/new models back to sampling system (304). In various embodiments, user may access existing and updated neural network models, and related data, in database (402) via for e.g. a web application as described herein.

Embodiments provide methods for performing fluid analysis. Methods may include using the fluid analysis system (100) described herein, including cooling system (302), sampling system (304), and analytical system (400) including command and control system (406) and database (402) described herein. In an exemplary embodiment, the method includes routing fluid through the removable and replaceable sampling system (304) described herein, collecting real-time data from the fluid via the sampling system (304), and processing and transmitting the real-time data to the analytical system (400) described herein connected to the sampling system (304). The method may include routing the fluid through a removable and replaceable cooling system (302) for cooling the fluid prior to being routed through the sampling system (304). In exemplary embodiments, the method may include receiving the real-time data via the command and control system (406) and processing it through a set of existing neural network models for the fluid in the database (402) for predictive analysis. The method may include updating the existing neural network models or building new neural network models if the real-time data does not correspond to any of the set of existing neural network models. The method may further include deploying the updated or new neural network models back to the sampling system (304).

Embodiments of the present disclosure may be utilized in a multitude of real-world applications and industries requiring fluid analysis, including but not limited to in oil and gas drilling rigs onshore and offshore, oil and gas pipelines, oil processing and chemical plants, offshore vessels, river work boats, freight trucks, any large commercial engines, and systems related to analysis of municipal water quality, remote water quality (well, rain water, aquifer, bottled), engine oil, hydraulic oil, transmission oil, coolant, fuel (in system and at station), milk bottling plants, beer kegging/bottling plants, industrial waste water, shipped crude oil, and/or urine.

Embodiments of the present disclosure may provide for more accurate real-time application data, increased resale value of equipment by providing history documentation in the cloud, improved oil analysis trending through better accuracy and consistency of sampling, low cost strategies to equip all critical systems, reduced current manpower demands, reduced risk-based costs and offering of failure prevention through root-cause monitoring, minimized operator exposure to safety and health hazards while sampling, reduced risk of spillages during sampling, and thus reduced H&S issues, particularly for users in the "Food-safe" oils industries, reduction/elimination of practice of disposal of samples and use of reagents at the laboratory, maximized information for optimum maintenance planning extending drain intervals, allowing for oil to stay in a clean state for longer periods per the NIST standards, extended oil drain intervals, improved reduction of solid, liquid, and/or gaseous contaminants from oils, increased engine and equipment life, and reduced operating costs.

While the embodiments are described with reference to various implementations and exploitations, it will be understood that these embodiments are illustrative and that the scope of the disclosures is not limited to them. Many variations, modifications, additions, and improvements are possible. Further still, any steps described herein may be carried out in any desired order, and any desired steps may be added or deleted.

What is claimed is:

1. A system for analyzing an oil, comprising:
  a sample chamber fluidically coupled to a source engine and configured to receive a portion of an oil circulating through the source engine;
  a laser optically coupled to the sample chamber and configured to generate and transmit a first electromagnetic radiation to the portion of the oil; and
  a Raman spectrometer optically coupled to the sample chamber and configured to detect a second electromagnetic radiation, emitted by the portion of the oil in response to the first electromagnetic radiation, and configured to generate a Raman spectrum from the second electromagnetic radiation.

2. The system of claim 1, further comprising:
  a removable and replaceable cooling system that is configured to cool the portion of the oil.

3. The system of claim 1, further comprising:
  a charge-coupled device (CCD) sensor that is configured to detect the second electromagnetic radiation.

4. The system of claim 1, further comprising:
  an analytical apparatus, including a processor circuit, which is configured to perform operations including:
    receiving a Raman spectrum from the Raman spectrometer; and
    determining a condition of the oil based on the Raman spectrum.

5. The system of claim 4, wherein the analytical apparatus further performs operations including:
  determining one or more of: a presence of a wear metal in the oil sample, a presence of an amount of an additive in the oil sample, a viscosity of the oil sample, a presence of water in the oil sample, a total acid number (TAN) of the oil sample, presence of coolant in the oil sample, a presence of fuel in the oil sample, a total base number (TBN) of the oil sample, a dilution of the oil sample, or a particle count of particulate matter within the oil sample.

6. The system of claim 1, wherein the laser is configured to generate the first electromagnetic radiation:
  having a wavelength ranging from about 250 nm to about 800 nm; or
  having a wavelength ranging from about 800 nm to about 1500 nm.

7. The system of claim 1, wherein the laser is at least one of an LED source, infrared source, near infrared source, visible source, UV source, and wavelength stabilized source.

8. The system of claim 1, wherein the source engine includes one or more of a two-stroke engine, a four-stroke engine, a reciprocating engine, a rotary engine, a compression ignition engine, a spark ignition engine, a single-cylinder engine, an in-line engine, a V-type engine, an opposed-cylinder engine, a W-type engine, an opposite-piston engine, a radial engine, a naturally aspirated engine, a supercharged engine, a turbocharged engine, a multi-cylinder engine, a diesel engine, a petrol engine, a gas engine, or an electric engine.

9. A fluid analysis system, comprising:
a fluid inlet configured to fluidically couple to a fluid source and to receive a fluid sample from the fluid source; and
a removable and replaceable sampling system comprising:
a sample chamber configured to fluidically couple to the fluid inlet and configured to receive the fluid sample from the fluid source;
an excitation source configured to generate incident electromagnetic radiation;
a Raman spectrometer; and
a probe optically coupled to the sample chamber, to the excitation source, and to the Raman spectrometer, the probe configured:
to receive the incident electromagnetic radiation from the excitation source and to transmit the incident radiation to the fluid sample; and
to receive scattered/emitted radiation by the fluid sample and to transmit the scattered/emitted radiation to the Raman spectrometer,
wherein the removable and replaceable sampling system is configured to be electrically and fluidically coupled to one or more additional removable and replaceable sampling systems.

10. The system of claim 9, further comprising:
a removable and replaceable cooling system that is configured to cool the fluid sample.

11. The system of claim 9, further comprising:
a charge-coupled device (CCD) sensor that is configured to detect the scattered/emitted radiation.

12. The system of claim 9, further comprising:
an analytical apparatus, including a processor circuit, which is configured to perform operations including:
receiving a Raman spectrum from the Raman spectrometer; and
determining a condition of the fluid sample based on the Raman spectrum.

13. The system of claim 12, wherein the analytical apparatus further performs operations including:
determining one or more of: a presence of a wear metal in the fluid sample, a presence of an amount of an additive in the fluid sample, a viscosity of the fluid sample, a presence of water in the fluid sample, a total acid number (TAN) of the fluid sample, presence of coolant in the fluid sample, a presence of fuel in the fluid sample, a total base number (TBN) of the fluid sample, a dilution of the fluid sample, or a particle count of particulate matter within the fluid sample.

14. The system of claim 9, wherein the excitation source is configured to generate the incident electromagnetic radiation:
having a wavelength ranging from about 250 nm to about 800 nm; or
having a wavelength ranging from about 800 nm to about 1500 nm.

15. The system of claim 9, wherein the excitation source is at least one of an LED source, infrared source, near infrared source, visible source, UV source, and wavelength stabilized source.

16. The system of claim 9, wherein the source engine includes one or more of a two-stroke engine, a four-stroke engine, a reciprocating engine, a rotary engine, a compression ignition engine, a spark ignition engine, a single-cylinder engine, an in-line engine, a V-type engine, an opposed-cylinder engine, a W-type engine, an opposite-piston engine, a radial engine, a naturally aspirated engine, a supercharged engine, a turbocharged engine, a multi-cylinder engine, a diesel engine, a petrol engine, a gas engine, or an electric engine.

17. A method for analyzing an oil, comprising:
receiving, by a sample chamber coupled to a source engine, a portion of an oil circulating through the source engine;
generating, by a laser device, a first electromagnetic radiation;
transmitting, by an optical probe optically connected to the laser device, the first electromagnetic radiation to the portion of the oil contained in the sample chamber;
receiving, by the optical probe, second electromagnetic radiation emitted by the portion of the oil in response to the first electromagnetic radiation;
transmitting, by the optical probe which is further optically connected to a Raman spectrometer, the second electromagnetic radiation to the Raman spectrometer; and
detecting a Raman spectrum emitted from the portion of the oil.

18. The method of claim 17, further comprising:
cooling, by a removable and replaceable cooling system, the portion of oil.

19. The method of claim 17, further comprising:
detecting, by a charge-coupled device (CCD) sensor, the second electromagnetic radiation.

20. The method of claim 17, further comprising:
generating, by the Raman spectrometer, a Raman spectrum of the oil.

21. The method of claim 20, further comprising:
receiving, by an analytical apparatus that includes a processor circuit, the Raman spectrum from the Raman spectrometer; and
determining a condition of the oil based on the Raman spectrum.

22. The method of claim 21, further comprising:
determining, by the analytical apparatus, one or more of:
a presence of a wear metal in the portion of the oil, a presence of an amount of an additive in the portion of the oil, a viscosity of the portion of the oil, a presence of water in the portion of the oil, a total acid number (TAN) of the portion of the oil, presence of coolant in the portion of the oil, a presence of fuel in the portion of the oil, a total base number (TBN) of the portion of the oil, a dilution of the portion of the oil, or a particle count of particulate matter within the portion of the oil.

23. The method of claim 21, further comprising:
performing a training process, by the analytical apparatus, to generate a model of a Raman spectrum based on known data; and
determining the condition of the oil based on the model and the received Raman spectrum.

24. A method of fluid analysis, comprising:
receiving, by a fluid inlet coupled to a fluid source, a fluid sample from the fluid source;
transmitting the fluid sample to a sample chamber of a removable and replaceable sampling system, the removable and replaceable sampling system being configured to be electrically and fluidically coupled to one or more additional removable and replaceable sampling systems;

generating, by an excitation source of the removable and replaceable sampling system, incident electromagnetic radiation;

transmitting, by an optical probe of the removable and replaceable sampling system, the incident electromagnetic radiation to the fluid sample;

receiving, by the optical probe, scattered/emitted radiation emitted by the fluid sample; and transmitting, by the optical probe which is further optically connected to a Raman spectrometer, the scattered/emitted radiation to the Raman spectrometer.

25. The method of claim 24, further comprising:

cooling, by a removable and replaceable cooling system, the portion of oil.

26. The method of claim 24, further comprising:

detecting, by a charge-coupled device (CCD) sensor, the scattered/emitted radiation.

27. The method of claim 24, further comprising:

generating, by the Raman spectrometer, a Raman spectrum of the fluid sample.

28. The method of claim 27, further comprising:

receiving, by an analytical apparatus that includes a processor circuit, the Raman spectrum from the Raman spectrometer; and determining a condition of the fluid sample based on the Raman spectrum.

29. The method of claim 28, further comprising:

determining, by the analytical apparatus, one or more of: a presence of a wear metal in the fluid sample, a presence of an amount of an additive in the fluid sample, a viscosity of the fluid sample, a presence of water in the fluid sample, a total acid number (TAN) of the fluid sample, presence of coolant in the fluid sample, a presence of fuel in the fluid sample, a total base number (TBN) of the fluid sample, a dilution of the fluid sample, or a particle count of particulate matter within the fluid sample.

30. The method of claim 28, further comprising:

performing a training process, by the analytical apparatus, to generate a model of a Raman spectrum based on known data; and determining the condition of the fluid sample based on the model and the received Raman spectrum.

* * * * *